(12) United States Patent
Joshi et al.

(10) Patent No.: US 12,383,117 B2
(45) Date of Patent: Aug. 12, 2025

(54) POWERED ENDOSCOPIC DEVICE WITH HAPTIC FEEDBACK

(71) Applicant: BOSTON SCIENTIFIC SCIMED, INC., Maple Grove, MN (US)

(72) Inventors: Sharmad S. Joshi, Auburndale, MA (US); Michael S. H. Chu, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 13 days.

(21) Appl. No.: 18/339,810

(22) Filed: Jun. 22, 2023

(65) Prior Publication Data

US 2023/0329526 A1    Oct. 19, 2023

Related U.S. Application Data

(63) Continuation of application No. 17/118,748, filed on Dec. 11, 2020, now Pat. No. 11,723,516.

(60) Provisional application No. 62/947,388, filed on Dec. 12, 2019.

(51) Int. Cl.
*A61B 1/00* (2006.01)
*A61B 1/05* (2006.01)

(52) U.S. Cl.
CPC ........ *A61B 1/00055* (2013.01); *A61B 1/0004* (2022.02); *A61B 1/00042* (2022.02); *A61B 1/00043* (2013.01); *A61B 1/00087* (2013.01); *A61B 1/00097* (2022.02); *A61B 1/00133* (2013.01); *A61B 1/00142* (2013.01); *A61B 1/00156* (2013.01); *A61B 1/0016* (2013.01); *A61B 1/05* (2013.01)

(58) Field of Classification Search
CPC ............ A61B 1/00087; A61B 1/00142; A61B 1/0016; A61B 1/05; A61B 1/00043; A61B 1/00133

See application file for complete search history.

(56) References Cited

U.S. PATENT DOCUMENTS

| | | | |
|---|---|---|---|
| 2001/0004676 A1 | 6/2001 | Ouchi | |
| 2005/0250989 A1* | 11/2005 | Suzuki | A61B 1/00133 600/106 |
| 2019/0208994 A1 | 7/2019 | Davis | |
| 2019/0209810 A1 | 7/2019 | Reid et al. | |
| 2020/0100647 A1 | 4/2020 | Craig et al. | |

(Continued)

*Primary Examiner* — Aaron B Fairchild
(74) *Attorney, Agent, or Firm* — Seager, Tufte & Wickhem, LLP

(57) ABSTRACT

An endoscopic deployment device includes a body mountable on an endoscopic device, the body having a movable carrier couplable to an end effector device, the end effector device having an end effector shaft covered by an outer sheath and an end effector extending from a distal end of the end effector shaft, the outer sheath being sized and shaped for insertion through a working channel of the endoscopic device, the body having a carrier channel for the carrier to slide therein, wherein the end effecter is actuatable between an open position and a closed position; and a motor having a drive shaft coupled to the carrier, rotation of the drive shaft sliding the carrier in the carrier channel and actuating the end effector in response to a signal from one or more actuation buttons; wherein at least one vibration motor generates vibrations as an angular position of the motor changes.

20 Claims, 17 Drawing Sheets

(56) References Cited

U.S. PATENT DOCUMENTS

2020/0345207 A1 11/2020 Nguyen et al.
2021/0085153 A1 3/2021 Chu et al.

* cited by examiner

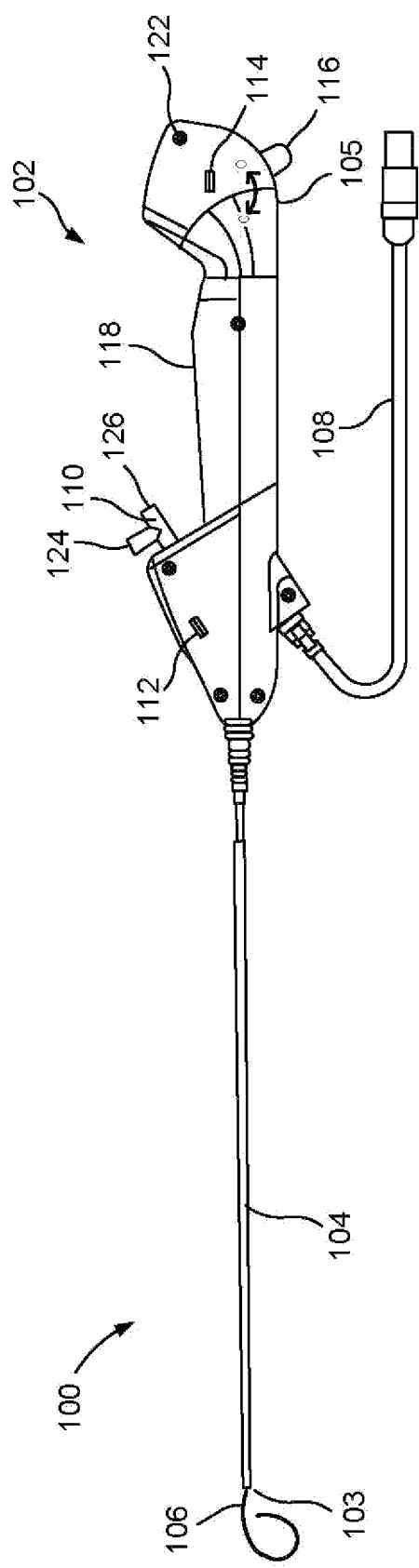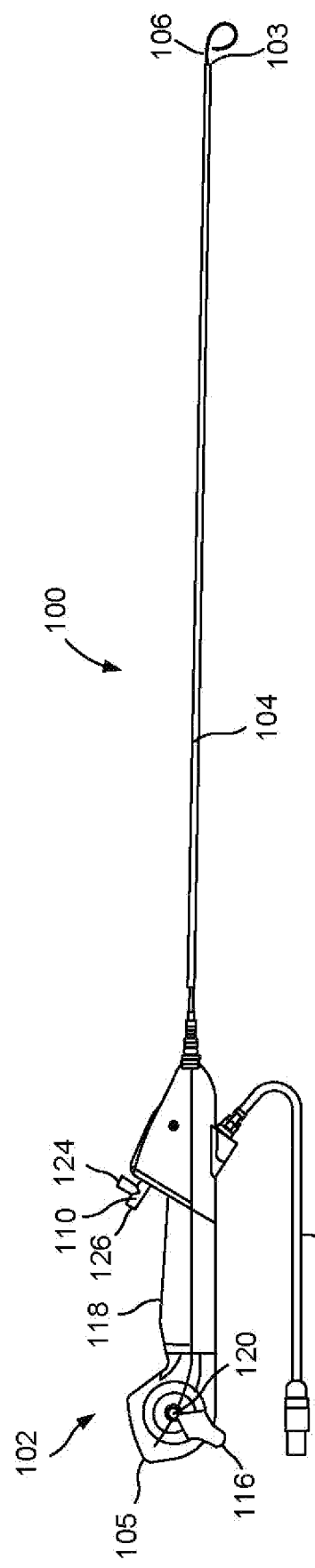
FIG. 1A
FIG. 1B

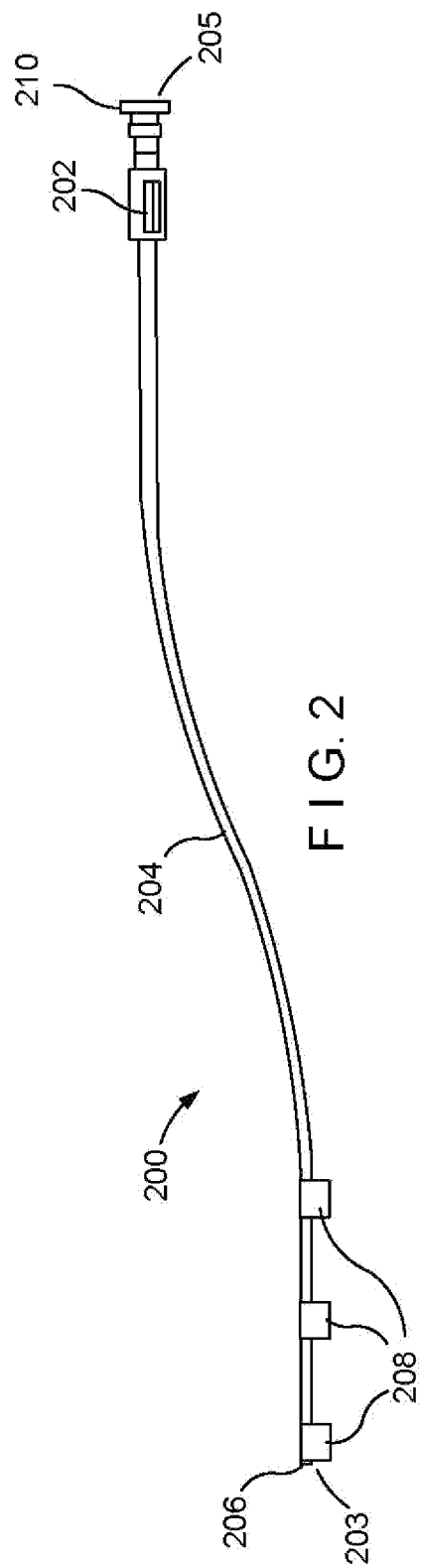
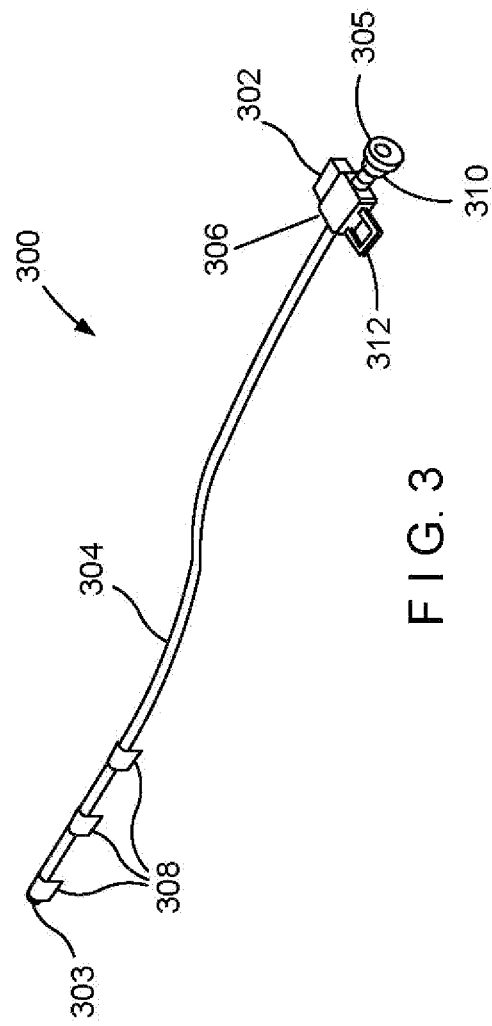

POWERED ENDOSCOPIC DEVICE WITH HAPTIC FEEDBACK

CROSS REFERENCE TO RELATED APPLICATIONS

The present application is a continuation of U.S. patent application Ser. No. 17/118,748, filed Dec. 11, 2020, which claims the benefit of and priority to U.S. Provisional Patent Application Ser. No. 62/947,388, filed on Dec. 12, 2019, the disclosures of which are incorporated herein by reference.

FIELD

The present disclosure relates to an endoscopic device and, in particular, an endoscope handle with powered features and/or accessories providing haptic feedback.

BACKGROUND

Various accessory devices may be used with an endoscopic device to perform various diagnostic and treatment procedures in the imaged cavity. However, the accessory devices may not always be compatible with the endoscopic device. For example, the physical configurations of the devices may be difficult to use in conjunction, or the devices may not be programmatically compatible.

SUMMARY

In a first example, an endoscopic deployment device may comprise a body mountable on an endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through a working channel of an endoscopic shaft of the endoscopic device, the body having a carrier channel sized for the carrier to slide therein, wherein the end effecter is actuatable between an extended open position and a retracted closed position by sliding the carrier in the carrier channel; and a motor having a drive shaft coupled to the carrier, rotation of the drive shaft sliding the carrier in the carrier channel and actuating the end effector in response to a signal from one or more actuation buttons. At least one vibration motor may generate vibrations as an angular position of the motor changes.

In addition or alternatively, the one or more actuation buttons is a button pad physically separate from the body of the endoscopic deployment device and in operable communication with the motor.

In addition or alternatively, wherein an intensity of the vibrations corresponds to the angular position of the motor.

In addition or alternatively, the intensity of the vibrations is linear relative to the angular position of the motor.

In addition or alternatively, the intensity of the vibrations is non-linear relative to the angular position of the motor.

In addition or alternatively, the motor is a stepper motor.

In addition or alternatively, the drive shaft has an arm extending orthogonally therefrom coupled to a slot in the carrier and the arm has a pin at an end of the arm opposite the drive shaft, the pin being coupled to the slot so that, when the drive shaft rotates, the pin slides in the slot in a direction orthogonal to the carrier channel and the carrier slides in the carrier channel.

In addition or alternatively, the drive shaft is a lead screw coupled to a threaded through-hole extending through a portion of the carrier parallel to the carrier channel so that, when the drive shaft rotates, the carrier slides in the carrier channel.

In addition or alternatively, a pinion gear is coupled to the drive shaft and to a rack that is an integral portion of the carrier so that, when the drive shaft rotates, the pinion gear drives the rack and the carrier slides in the carrier channel.

In addition or alternatively, the end effector device is a retrieval device for capturing objects at a distal end of the endoscopic shaft.

In addition or alternatively, the end effector device is a laser fiber for fragmenting or cauterizing objects at a distal end of the endoscopic shaft.

In addition or alternatively, and in another example, an endoscopic device may comprise an elongated flexible endoscopic shaft including a working channel and a deflectable distal tip, the flexible endoscopic shaft being sized and shaped for insertion to a target site, the distal tip including a camera; and a handle from which the endoscopic shaft extends distally, the handle including a pull wire wheel disposed therein, the pull wire wheel comprising pull wire attachments from which first and second pull wires extend distally through the endoscopic shaft to the distal tip. Rotation of the pull wire wheel may deflect the distal tip by tensioning a first one of the first and second pull wires and slacking a second one of the first and second pull wires, the handle including a motor disposed within the handle, the motor having a rotatable drive shaft coupled to and configured to rotate the pull wire wheel in response to a signal from one or more actuation buttons. At least one vibration motor may generate vibrations as an angular position of the motor changes.

In addition or alternatively, an intensity of the vibrations corresponds to the angular position of the motor.

In addition or alternatively, the motor is a stepper motor.

In addition or alternatively, the endoscopic device may further comprise an endoscopic deployment device, the endoscopic deployment device comprising: a body mounted on the handle of the endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through the working channel of the endoscopic shaft of the endoscopic device, the body having a carrier channel sized for the carrier to slide therein, wherein the end effecter is actuatable between an extended open position and a retracted closed position by sliding the carrier in the carrier channel; and a motor having a drive shaft coupled to the carrier, rotation of the drive shaft sliding the carrier in the carrier channel and actuating the end effector in response to a signal from one or more actuation buttons. At least one vibration motor may generate vibrations as an angular position of the motor changes.

In addition or alternatively, and in another example, an endoscopic device may comprise an elongated flexible endoscopic shaft including a working channel and a deflectable distal tip, the flexible endoscopic shaft being sized and shaped for insertion to a target site, the distal tip including a camera; a handle from which the endoscopic shaft extends distally, the handle including a motor disposed within the handle and operably connected to the distal tip, the motor being configured to deflect the distal tip in response to a signal from a lever coupled to the handle; wherein a first vibration motor is configured to generate vibrations within the lever as an angular position of the motor within the handle changes; and a body mounted on the handle, the body having a movable carrier couplable to an elongated end effector device, the elongated end effector device having an end effector shaft covered by an outer sheath and an end effector extending from a distal end of the end effector shaft, the outer sheath being sized and shaped for insertion through the working channel of the endoscopic shaft, the body having a carrier channel sized for the carrier to slide therein. The body may include a motor having a drive shaft coupled to the carrier, wherein rotation of the drive shaft slides the carrier in the carrier channel and actuates the end effector in response to a signal from one or more actuation buttons on the handle. The handle may further include at least one vibration motor configured to generate vibrations within the one or more actuation buttons as an angular position of the motor within the body changes.

In addition or alternatively, the at least one vibration motor includes a second vibration motor coupled to a first actuation button of the one or more actuation buttons and a third vibration motor coupled to a second actuation button of the one or more actuation buttons.

In addition or alternatively, the second vibration motor is configured to generate vibrations within the first actuation button when the end effector is actuated toward a retracted closed position; and the third vibration motor is configured to generate vibrations within the second actuation button when the end effector is actuated toward an extended open position.

In addition or alternatively, an intensity of the vibrations within the first actuation button increases as the end effector approaches the retracted closed position, and an intensity of the vibrations within the second actuation button increases as the end effector approaches the extended open position.

In addition or alternatively, an intensity of the vibrations within the lever increases as deflection of the distal tip away from a central longitudinal axis of the endoscopic shaft increases.

The above summary of some embodiments, aspects, and/ or examples is not intended to describe each disclosed embodiment or every implementation of the present disclosure. The Figures, and Detailed Description, which follow, more particularly exemplify these embodiments.

BRIEF DESCRIPTION OF THE DRAWINGS

FIG. 1A shows a front view of an endoscopic device compatible with powered accessories according to various exemplary embodiments of the present disclosure.

FIG. 1B shows a rear view of the endoscopic device of FIG. 1A.

FIG. 2 shows a pressure sensor device configured for compatibility with the endoscopic device of FIG. 1A.

FIG. 3 shows a flow sensor device configured for compatibility with the endoscopic device of FIG. 1A.

Figure 4A:
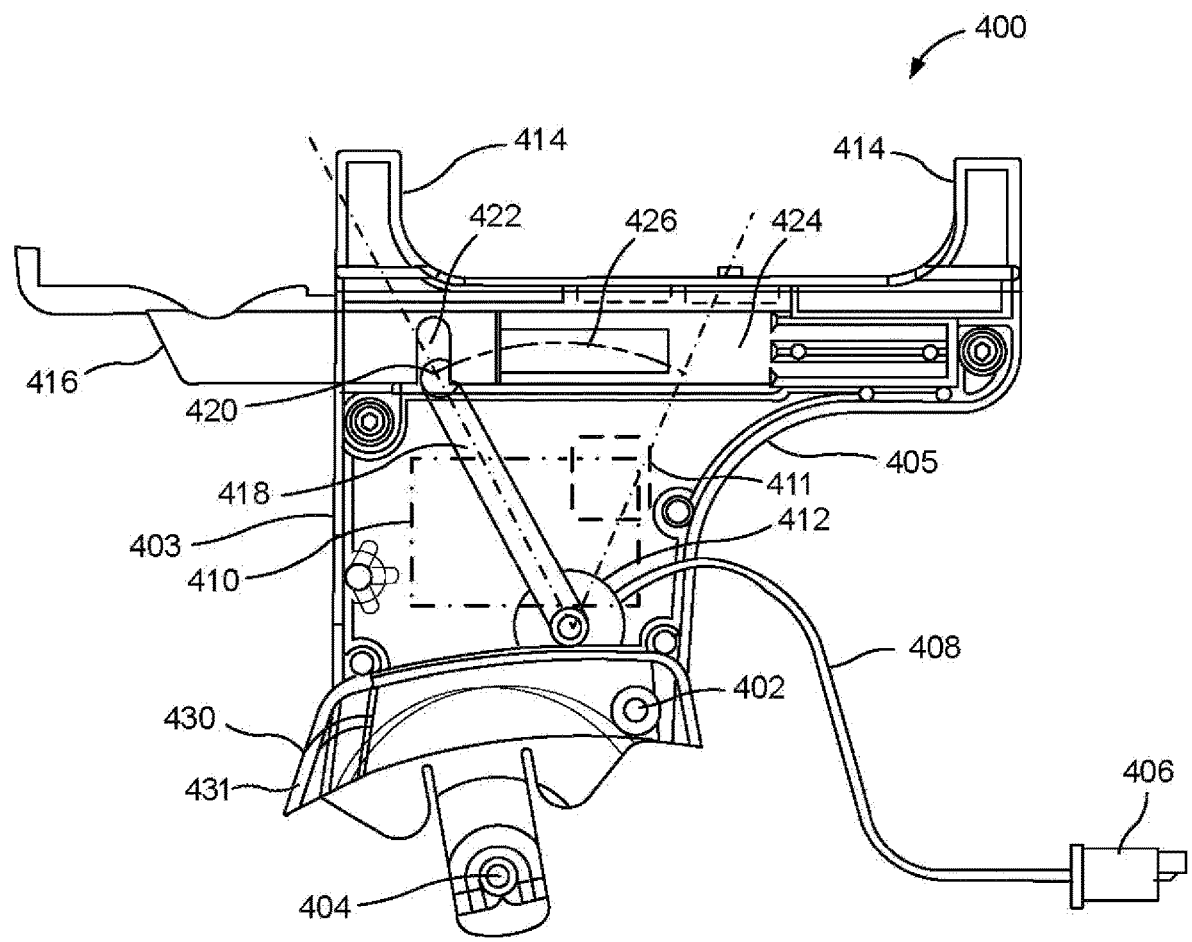
FIG. 4A shows a transparent side view of a first embodiment of a motorized deployment device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications may be disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, some instances of some elements or features may not be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some exemplary embodiments describe an endoscopic device (e.g., endoscope) having a scope handle with one or more external communication interfaces (e.g., USB ports) and accessory devices compatible with the endoscope and pluggable thereinto. For example, the accessory devices may include a pressure sensor, a temperature sensor, a flow sensor, an additional camera, an additional light, an optical sensor, a catheter, a laser time-of-flight distance sensor, a deployment device, other sensors or combinations thereof.

In another embodiment, an accessory device is described that is a motorized endoscopic deployment device for controlling an elongated end effector device to capture e.g. kidney stones or the like. The motorized deployment device is compatible with the endoscope or may be integrated with the endoscope in a monolithic handle. The elongated end effector device refers to any one of a number of devices compatible with and actuated by the motorized deployment device. For example, the elongated end effector device may be the retrieval device for capturing kidney stones, a laser fiber device, a therapy needle, snares, forceps, band ligation devices, etc. Any of the elongated end effector devices may be fitted with, for example, a handle sized and shaped to be used with the motorized deployment device. Thus, any elongated end effector device compatible with and fitted with an appropriate handle (or a similar device) may also be used with the motorized deployment device.

In still another embodiment, the endoscope handle has a motor for controlling articulation of the distal tip of the endoscopic shaft. The motor may be, e.g., a stepper motor allowing for precise positioning and holding of the shaft tip and/or precise control of the end effector feature of the elongated end effector device. The motor may be internal to the handle or may be externally coupled to the handle, e.g., connected by a flexible drive shaft extension or the like.

In each of the embodiments, the communication interfaces between the scope handle and the accessory device(s), whether internal or via external communication interfaces, are arranged so that an operating physician may operate the articulation of the distal shaft tip and control the accessory device in an ergonomic manner. For example, in one embodiment, where the motorized deployment device is connected to the scope handle, the deflection knob for the distal tip of the endoscopic shaft and a button control for the motorized deployment device are arranged so that both may be operated simultaneously or independently without overstressing the physician's hand. In another embodiment, where the motorized deployment device is monolithic with or otherwise compatible with the scope handle, a button pad may be used to operate both the distal tip of the endoscopic shaft and the elongated end effector device. The button pad may include, for example, four momentary buttons located on the bottom side of the scope handle and may be operated by the physician's grip hand thumb. Depressing a button causes a movement to occur to the scope shaft or the end effector, and releasing the button causes the stepper motor to stop and hold the current position. In another embodiment, a non-momentary button may be used such as a typical on/off switch. In another embodiment, one or more actuation buttons may be disposed on and/or may be a part of the handle (for example, a thumb lever and/or buttons operable by a user's grip hand fingertips). In still another embodiment, control is fully implemented remotely from the devices via, e.g., a console. Other configurations are also contemplated.

Some embodiments have a data bus in the scope handle where data may be received via the various accessory devices and control for the devices may be implemented. The handle may be coupled to an endoscopic console or the like via a cable, with data from the devices being sent thereto or control of the devices being implemented therefrom. In some embodiments, the handle may be electronically connected to the endoscopic console or the like using one or more wireless technologies (e.g., Wi-Fi, Bluetooth, etc.). In some embodiments, data from one of the accessory devices and/or the endoscope may be used to control the operation of another one of the accessory devices and/or the endoscope. For example, a reading from a pressure sensor may trigger an operation of an irrigation mechanism. In another example the output from a laser-distance sensor may adjust/optimize the distance from a laser fiber tip to a ureteral stone via the stepper motor to maximize laser efficiency during stone fragmentation. In another embodiment the data from an accessory device is displayed on e.g. a monitor screen for the physician to evaluate and react accordingly.

FIGS. 1A-1B show a front view and a rear view of an endoscopic device 100 compatible with powered and data accessories according to various exemplary embodiments of the present disclosure. The endoscopic device 100 may be specific to a particular endoscopic procedure, such as, e.g., ureteroscopy, or may be a general-purpose device suitable for a wide variety of procedures. The endoscopic device 100 includes a handle 102 connected to an endoscopic shaft 104 with a deflectable distal tip 106 at a distal end 103. The distal tip 106 has a camera and may, for example, have full 270° deflection capabilities in more than one direction for viewing patient anatomy as would be understood by those skilled in the art.

The handle 102 of the endoscopic device 100 has a plurality of elements configured to facilitate the endoscopic procedure. A cable 108 extends from the handle 102 and is configured for attachment to an electronic device (not pictured) such as e.g. a computer system, a console, a microcontroller, etc. for providing power, analyzing endoscopic data, controlling the endoscopic intervention, or performing other functions. The electronic device to which the cable 108 is connected may have functionality for recognizing and exchanging data with other endoscopic accessories, to be described in detail below. The handle 102 has a grip area 118 for the operating physician to grasp while performing the endoscopic procedure. A deflection knob 116 at a proximal end 105 of the device may be actuated to control the deflection of the distal tip 106 as would be understood by those skilled in the art. Even when an endoscopic device 100 has a motorized deflection means, to be described in detail below, a short handle version of the deflection knob 116 is present, in this embodiment, for manually straightening the distal tip 106 and removing the 104 endoscopic shaft 104 from the patient anatomy in case of e.g. power failure.

The handle 102 further has at least one communication interface for attaching accessory devices. In the present embodiment, the handle 102 has a first communication interface 112 and second communication interface 114 that are, in this embodiment, Universal Serial Bus type-C (USB-C) ports. However, more or less communication interface of various types, including, for example, custom interfaces, may be used. In other embodiments, the handle 102 has only one communication interface but may receive e.g. a USB hub with multiple ports for connecting multiple accessories. The communication interfaces 112, 114 may provide power to the accessory devices in addition to exchanging data therewith. Thus, the accessory devices need not have separate cables running to the console or a battery that adds additional weigh to the handle 102. The accessory device may be uniquely associated with the endoscopic device 100 and recognized by the console through "plug and play" functionality without any user setup required.

A T-connector 110 extends from a distal portion of the handle 102 and provides first and second ports 124, 126 for accessing the working channel of the endoscopic shaft 104. In this embodiment, the first and second ports 124, 126 are arranged perpendicularly to one another with the first port 124 facing distally and the second port 126 facing proximally. An accessory device or an elongated end effector device may be passed through either one of the first and second ports 124, 126, however, the second port 126 may be preferred when the device is proximal to the T-connector 110. In another embodiment, a Y-connector is used with first and second ports both facing proximally, such that two devices may be passed into the working channel of the endoscopic shaft 104 from a position proximal to the Y-connector.

Various accessory devices may be mated with either of the two communication interfaces 112, 114, however, certain of the accessory devices are more compatible with either one of the two interfaces 112, 114. The first communication interface 112 is located distally on the handle 102. Certain of the accessory devices have corresponding communication interfaces, e.g., male USB-C ports, extending from the devices that lend themselves to spatial compatibility with the first communication interface 112.

For example, FIG. 2 shows a pressure sensor device 200 configured for compatibility with the endoscopic device 100, particularly with the first communication interface 112 of the endoscopic device 100. The pressure sensor device 200 has a communication interface 202 that may be mated with, e.g., inserted into, the first communication interface 112 of the endoscopic device 100. The pressure sensor device 200 has a shaft 204 extending from a proximal end 205 of the pressure sensor device 200 to a distal end 203 of the pressure sensor device 200. The shaft 204 has a through-lumen, i.e., channel, extending through its length. The proximal end of the shaft 204 has a female luer hub 210 extending therefrom and the communication interface 202 adjacent thereto. The communication interface 112 of the endoscopic device 100 is angled so that when the pressure sensor device 200 is attached to the endoscopic device 100, the female luer hub 210 is oriented in a manner similar to the second port 126 of the T-connector 110. Thus, the pressure sensor device 200 is more easily coupled with a male luer port for e.g. fluid communication during use.

The pressure sensor device 200 has a pressure sensor 206 at a distal end of the shaft 204 and a plurality of clips 208 adjacent thereto for securing the shaft 204 of the pressure sensor device 200 to the endoscopic shaft 104. Although the present embodiment uses the clips 208, the shaft 204 may be secured to the endoscopic shaft 104 by other means such as, e.g., holders or the like.

As noted above, the pressure sensor device 200 may also be mated with the second communication interface 114 of the endoscopic device 100. However, in the presently described embodiment, mating with the first communication interface 112 is preferable in view of the ease with which the shaft 204 of the pressure sensor device 200 may be clipped to the endoscopic shaft 104 of the endoscopic device 100 as well as the positioning of the female luer hub 210.

In another example, FIG. 3 shows a flow sensor device 300 configured for compatibility with the endoscopic device 100, particularly with the first communication interface 112 of the endoscopic device. Similar to the pressure sensor device 200, the flow sensor device 300 has a communication interface 302 that may be mated with the first communication interface 112 of the endoscopic device 100. The flow sensor device 300 has a shaft 304 extending from a proximal end 305 of the flow sensor device 300 to a distal end 303 of the flow sensor device 300. The shaft 304 has a through-lumen extending through its length. The proximal end of the shaft 304 has a female luer hub 310 extending therefrom, the communication interface 302 adjacent thereto and a handle 312. Similar to the pressure sensor device 200, the flow sensor device 300 is easily coupled with a male luer port for fluid communication or any other reason.

The flow sensor device 300 has a flow sensor 306 adjacent to the handle 312 and a plurality of clips 308 adjacent to a distal end of the shaft 304 for securing the shaft 304 of the flow sensor device 300 to the endoscopic shaft 104. Similar to the pressure sensor device 200, the flow sensor device 300 may use attachment means other than the clips 308 such as, e.g. holders or the like. The pressure sensor device 200 may also be mated with the second communication interface 114 of the endoscopic device 100, however, mating with the first communication interface 112 is preferable in view of the spatial benefits discussed above.

Returning to FIGS. 1A and 1B, the second communication interface 114 is positioned proximally on the handle 102 and is compatible with accessory devices configured for insertion through a working channel of the endoscopic shaft 104 via, for example, the second port 126. For example, an accessory device such as an additional camera, an additional light, an optical sensor, or other device may be mated with the second communication interface 114 and inserted into the working channel. In this way, the cables/shafts of the devices are out of the way of the operating physician and can be used without significant bending of the accessory. However, these devices may also have a flexible cable that is inserted into the first communication interface 112 and flexed into the working channel without damaging the cable. Because the second communication interface 114 is proximal to the T-connector 110, with the second port 126 of the T-connector 110 directed proximally, there may be instances where a fluid being used during a ureteroscopic procedure leaks and/or splashes proximally. Thus, the proximal second communication interface 114 may have a fluid seal such as a Tuohy borst adapter or other configuration. The console cable 108 of the endoscopic device 100 may be associated with one of the communication interfaces 112, 114 such that an interface on the handle 102 is not necessary. For example, the cable 108 may be bifurcated and have an interface, e.g., USB port, extending from the bifurcated part of the cable 108.

The handle 102 of the endoscopic device 100 in the present embodiment has two mount holes 120, 122 positioned to couple to, for example, a motorized endoscopic deployment device 400 compatible with an elongated end effector device. The elongated end effector device may be any one of a number of devices having a variety of purposes such as, e.g., capturing and removing objects such as kidney stones, to be explained in further detail below.

Figure 4B:
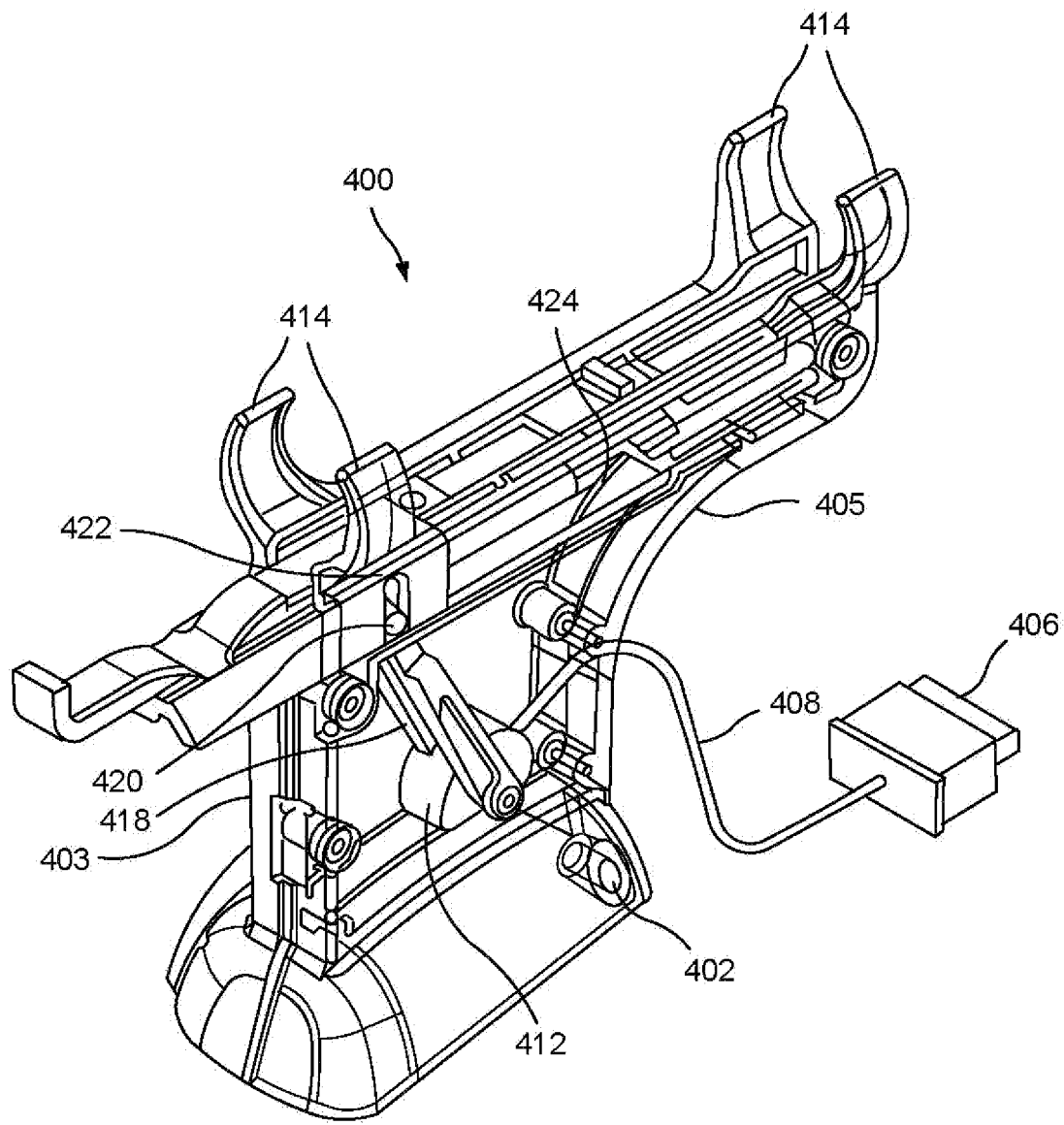
FIG. 4B shows a transparent perspective view of the motorized deployment device of FIG. 4A.

FIG. 4A shows a transparent side view and FIG. 4B shows a transparent perspective view of the motorized endoscopic deployment device 400. The motorized endoscopic deployment device 400 may be coupled to the endoscopic device 100 at the mount holes 120, 122 with corresponding mount pins 402, 404. The endoscopic deployment device 400 has a communication interface 406 that may be mated with, e.g., inserted into, the second communication interface 114 of the endoscopic device 100. The communication interface 406 may be, e.g., a male USB-C port. The communication interface 406 is connected via a flexible cable 408 to a control board 410 for a motor 412. The control board 410 includes an electrical port, in this case for connecting a USB, driver circuitry and motor terminals for connecting the motor 412. The motor 412 may be, e.g., a stepper motor. The motor 412 may be actuated by a signal provided by one or more actuation buttons 430 (or alternately, the button pad 1200 shown in FIG. 12, the first actuation button 1210 and the second actuation button 1212 shown in FIG. 12A, etc.). In another embodiment, the signal is generated in response to an endoscopic sensor reading. If the flexible cable 408 is sufficiently long the communication interface 406 may be mated with the first communication interface 112 of the endoscopic device 100, however, in the presently described embodiment, the motorized endoscopic deployment device 400 is particularly suited for connection via the second communication interface 114. In some embodiments, connection to the endoscopic deployment device 400 via one of the communication interfaces 112, 114 allows for actuation of the endoscopic deployment device 400 via controls on the handle 102.

The motorized endoscopic deployment device 400 has a handle coupler 414 extending from a distal end 403 of the endoscopic deployment device 400 to a proximal end 405 of the endoscopic deployment device 400. The handle coupler 414 is configured to receive a handle of the elongated end effector device, to be described below with respect to FIGS. 6-7. The elongated end effector device comprises a pull wire and an outer sheath to be fed through the working channel of the endoscopic shaft 104 via the T-connector 110 of the endoscopic device 100 or other embodiments of the endoscopic device. The elongated end effector device includes a handle at the proximal end and an end effector at the distal end of the pull wire, the end effector being actuatable by a slide on the handle between an extended open position and a retracted closed position for, for example, grasping objects or extending/retracting a laser fiber or a therapy needle during the endoscopic procedure. In an alternate embodiment, the elongated end effector device and the motorized endoscopic deployment device 400 are fashioned in a single monolithic unit. The end effector is actuatable via linear motion of a carrier 416 coupled to the slide of the elongated end effector device handle, to be described in detail below. For example, when the elongated device handle is inserted into the handle coupler 414, distal movement of the carrier 416 may cause the slide of the elongated end effector device to close the end effector, while proximal movement of the carrier 416 may cause the end effector to open. The motion of the carrier 416 is implemented via the motor 412 via an actuation linkage internal to the endoscopic deployment device 400, to be described below.

The carrier 416 of the endoscopic deployment device 400 is configured to slide within a carrier channel 424 of the endoscopic deployment device 400. The carrier channel 424 prevents any movement other than the proximal and/or distal sliding. The carrier 416 has a slot 422 where a pin 420 is configured to slide, the pin 420 being connected to the motor 412 via an arm 418. When the motor 412 is actuated the arm 418 is caused to rotate about a predefined arc 426. The linkage of the pin 420 with the slot 422 translates the angular motion of the arm 418 into linear motion of the carrier 416. The slot 422 allows the pin 420 to translate slightly in a direction orthogonal to the proximal/distal direction while driving the carrier 416 in the proximal/distal direction. When the carrier 416 is brought to its most distal position the end effector is fully closed (e.g., the retracted closed position), and when the carrier 416 is brought to its most proximal position the end effector is fully open (e.g., the extended open position), with varying degrees of openness/closedness between its most distal and most proximal positions.

The endoscopic deployment device 400 has one or more actuation buttons 430 for controlling movement of the carrier 416 via the control board 410 and the motor 412. The control board 410 may direct the motor 412 to rotate and/or to change its angular position based on signals from the one or more actuation buttons 430. The endoscopic deployment device 400 preferably has at least two actuation buttons 430. For example, a first button may be depressed to advance the carrier in the distal direction and stop when the button is released. A second button may be depressed to advance the carrier in the proximal direction and stop when the button is released. A double tap of either button (e.g., the first button or the second button) may bring the carrier to its most distal or most proximal position, respectively. Other button depression configurations may, for example, increase or decrease a speed of the carrier motion. In some embodiments, the endoscopic deployment device 400 may include at least one vibration motor 431 configured to generate vibrations as an angular position of the motor 412 changes to provide haptic feedback to the user. When using a powered accessory and/or device, tactile feedback normally associated with manual operations may not be available or felt by the user. Haptic feedback provided in accordance with the disclosure addresses the loss of tactile feedback associated with using powered accessories and/or devices, thereby restoring feedback to the user. The at least one vibration motor 431 may be positioned in proximity to (e.g., attached to, disposed under, etc.) the one or more actuation buttons 430 such that the user can feel the vibrations generated by the vibration motor 431 with the user's finger contacting the associated actuation button 430. In at least one embodiment, each of the one or more actuation buttons 430 may have one corresponding and/or adjacent vibration motor 431. In other embodiments, the vibration motor(s) 431 may be positioned at a different location of the endoscopic deployment device 400, if desired. In some instances, the user can detect an audible change in tone/sound resonating from the vibration motor(s) 431 to provide feedback. In some embodiments, the endoscopic deployment device 400 may include a vibration motor control board 411 configured to control the at least one vibration motor 431 in response to signals from the one or more actuation buttons 430 and/or the position of the carrier 416. In some embodiments, the control board 410 may also control the at least one vibration motor 431.

Figure 15:
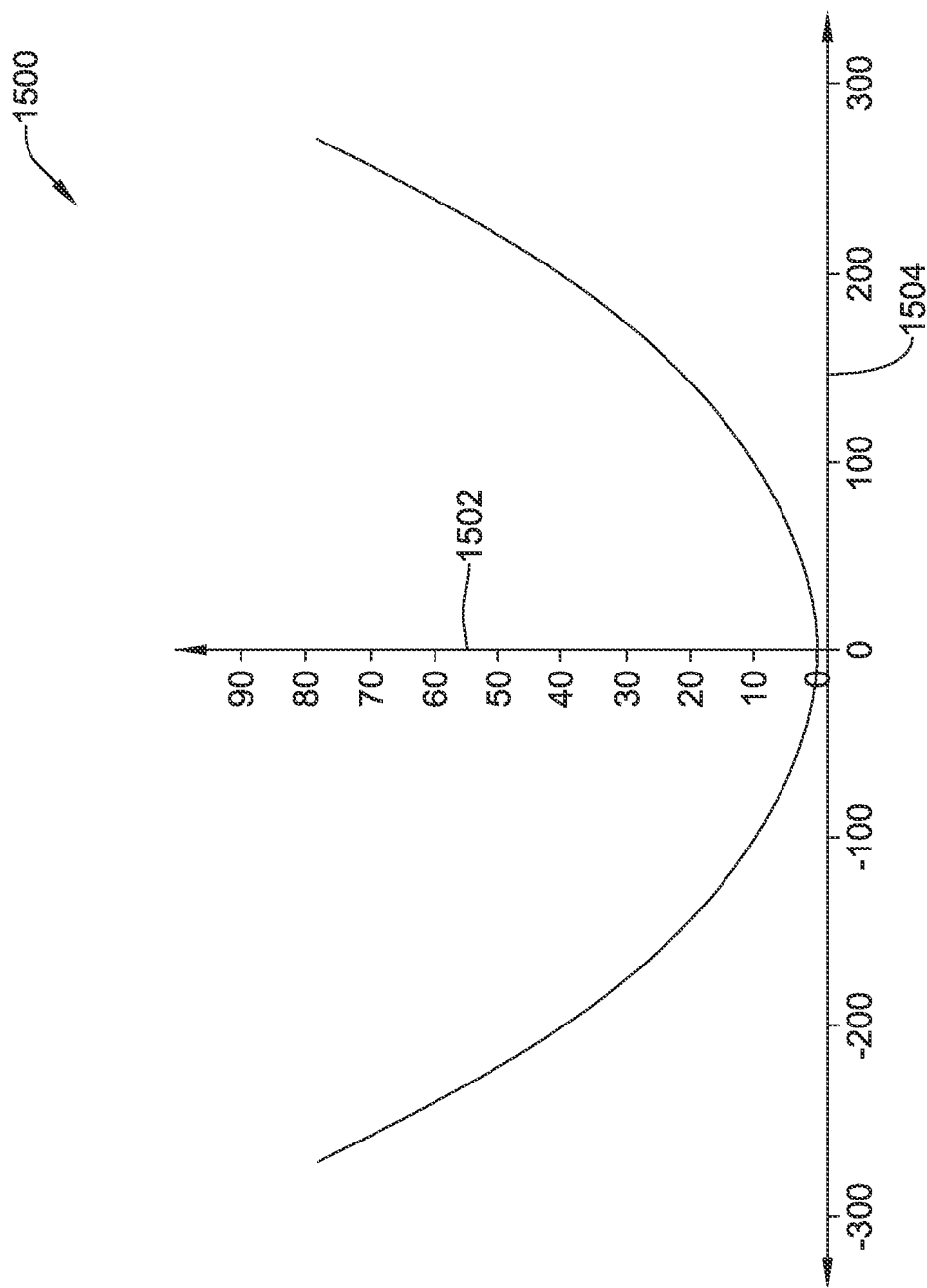
FIG. 15 is graph showing one example configuration of vibration intensity versus motor angle.
Figure 16:
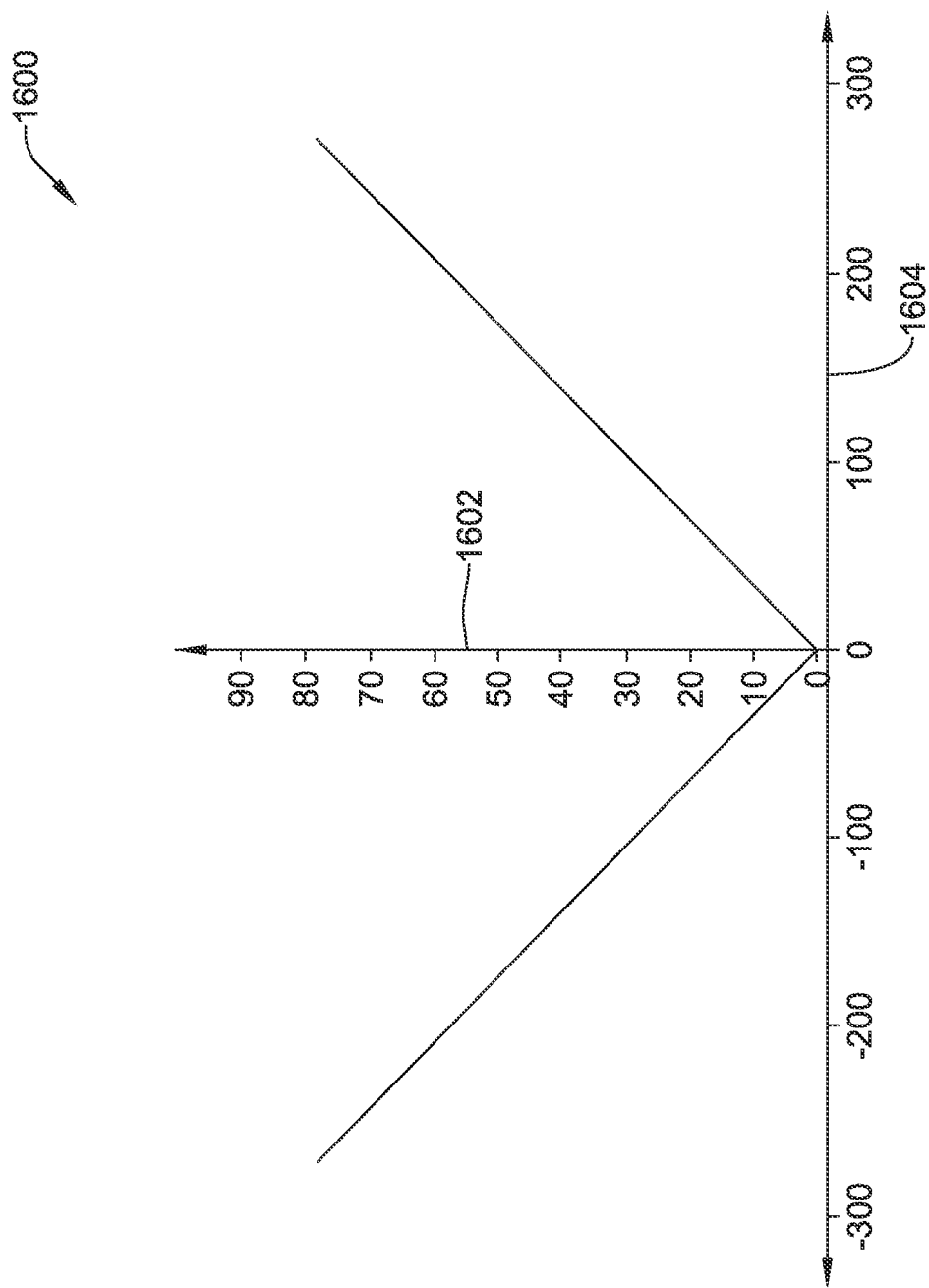
FIG. 16 is a graph showing another example configuration of vibration intensity versus motor angle.

In some embodiments, an intensity of the vibrations corresponds to the angular position of the motor 412 and/or the linear position of the carrier 416. Thus, the intensity of the vibrations may correspond with the degree that the end effector is open or closed. In some embodiments, the intensity of the vibrations is non-linear relative to the angular position of the motor 412, as illustrated in FIG. 15 for example. In some embodiments, the intensity of the vibrations is linear relative to the angular position of the motor 412, as illustrated in FIG. 16 for example. Thus, in some embodiments, the intensity of the vibrations changes (e.g., increases or decreases) as the end effector is opened to a greater extent and/or the intensity of the vibrations changes (e.g., decreases or increases) as the end effector is closed to a greater extent. Thus, the intensity of the vibrations may provide the user with hepatic feedback regarding the current state of the end effector or other device coupled to the carrier 416.

Placement of the one or more actuation buttons 430 adjacent to the grip area 118 and/or deflection knob 116 of the endoscopic device 100 (e.g., when the endoscopic deployment device 400 is attached, coupled, and/or mounted to the handle 102 of the endoscopic device 100) provides ergonomic benefits to the user of the devices. For example, a typical user may have difficulty operating an endoscopic deployment device and a distal tip deflection mechanism simultaneously, especially when the thumb is extended on the deflection knob 116 at full deflection, and especially if the user has a small hand. The spatial configuration of the endoscopic device 100 and the endoscopic deployment device 400 allow for ease of use due to the proximity of the one or more actuation buttons 430, the deflection knob 116, and/or the grip area 118.

In an alternate embodiment, voice commands may be implemented for controlling the end effector, such as, but not limited to, "open," "close," "stop," "faster," "slower," "load," etc.

Figure 5A:
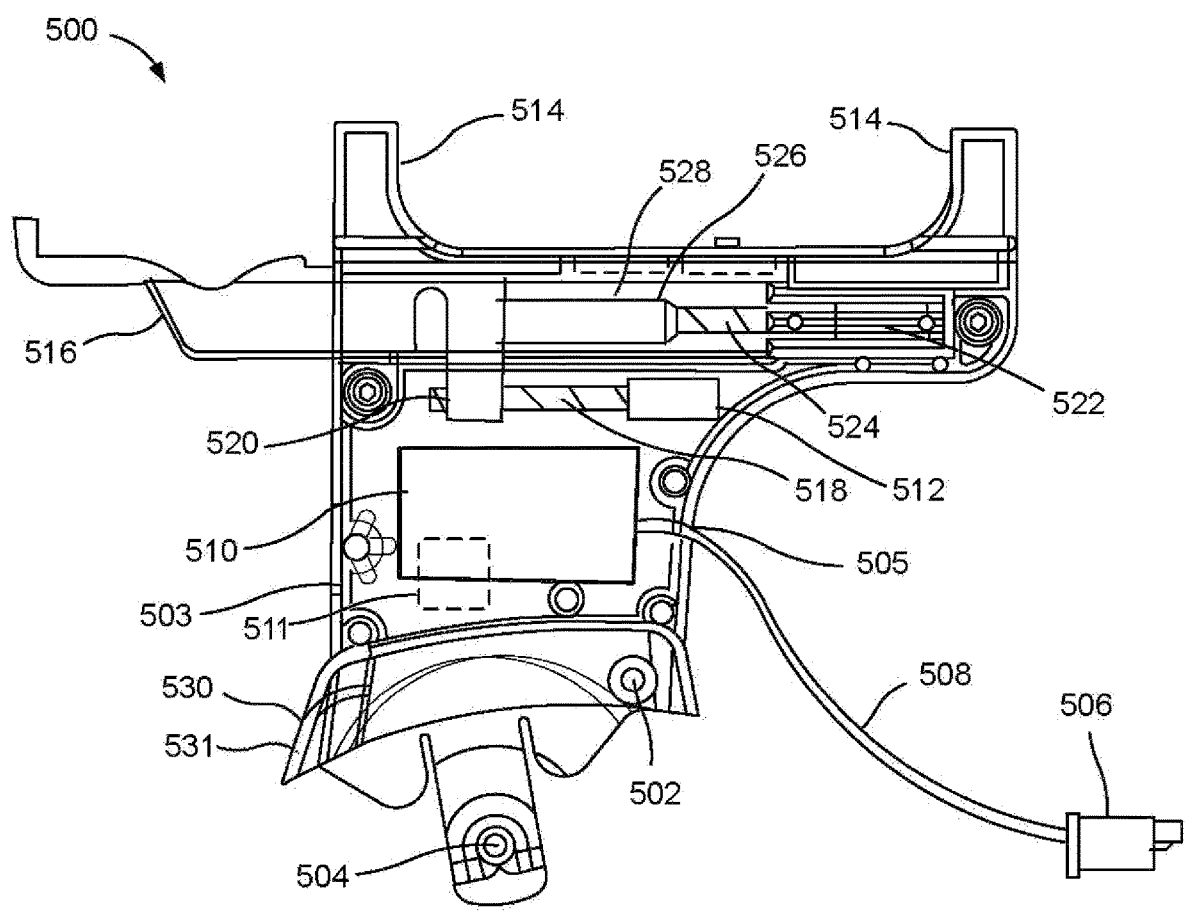
FIG. 5A shows a transparent side view of a second embodiment of a motorized deployment device.
Figure 5B:
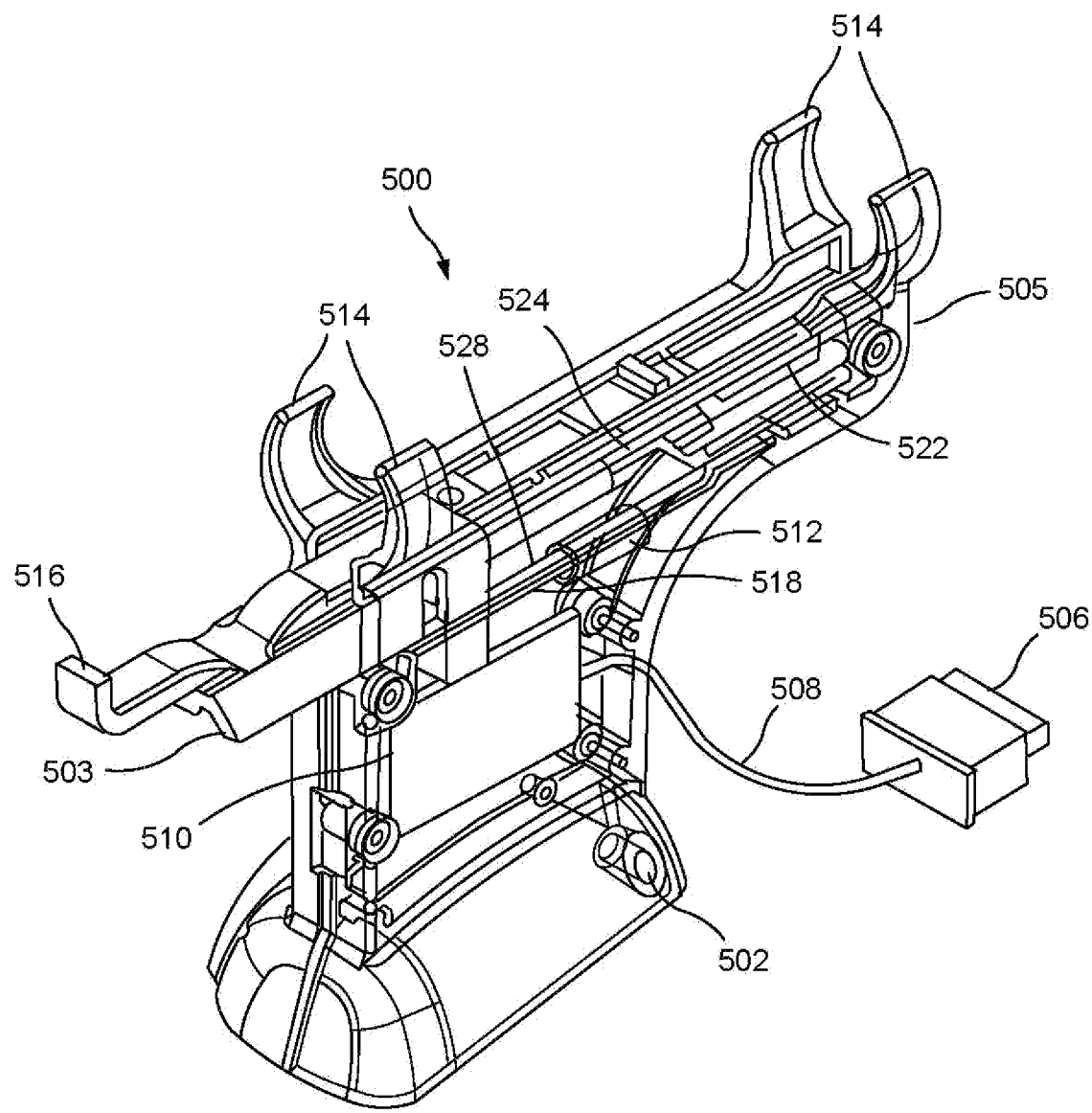
FIG. 5B shows a transparent perspective view of the motorized deployment device of FIG. 5A.

In an alternate embodiment, as shown in FIGS. 5A-5B, an endoscopic deployment device 500 extends from a distal end 503 to a proximal end 505 and may drive a carrier 516 using a lead screw in lieu of the linkage described with respect to the endoscopic deployment device 400. Similar to the endoscopic deployment device 400, the endoscopic deployment device 500 has mount pins 502, 504 for attaching the endoscopic deployment device 500 to the endoscopic device 100. Additionally, a communication interface 506, a flexible cable 508, a driver and control board 510, a handle coupler 514, the carrier 516 and a carrier channel 528 are substantially similar to those described with respect to the endoscopic deployment device 400. However, the endoscopic deployment device 500 has two location options for a motor 512, both of which are coupled to lead screws, i.e. screws used as a linkage to translate rotational motion into linear motion.

In some embodiments, the motor 512 is disposed at a location adjacent to and oriented parallel to the carrier channel 528 housing the carrier 516. When the motor 512 is actuated, a lead screw 518 extending from the motor is rotated. The lead screw 518 is coupled to a threaded through-hole 520 extending through a portion of the carrier 516. Thus, as the lead screw 518 is rotated, the carrier 516 is driven in a proximal/distal direction. In some embodiments, a second motor 522 is disposed at a location proximal to the carrier channel 528 housing the carrier 516. A lead screw 524 extends from the second motor 522 and is coupled to a threaded through-hole 526 extending through a proximal portion of the carrier 516. The second motor 522 drives the carrier 516 in a substantially similar manner as the motor 512.

In another alternate embodiment, the endoscopic deployment devices 400, 500 may implement a rack and pinion mechanism to drive the linear motion of the carrier 416, 516. A pinion gear may be attached to the drive shaft of the motor 412, 512, 522 and the rack may be attached to and/or may be an integral portion of the carrier 416, 516.

The endoscopic deployment device 500 may include one or more actuation buttons 530, similar to the one or more actuation buttons 430 of the endoscopic deployment device 400, for controlling movement of the carrier 516 via the control board 510 and the motor 512, 522. The control board 510 may direct the motor 512, 522 to rotate and/or to change its angular position based on signals from the one or more actuation buttons 530. The endoscopic deployment device 500 preferably has at least two actuation buttons 530. For example, a first button may be depressed to advance the carrier in the distal direction and stop when the button is released. A second button may be depressed to advance the carrier in the proximal direction and stop when the button is released. A double tap of either button (e.g., the first button or the second button) may bring the carrier to its most distal or most proximal position, respectively. Other button depression configurations may, for example, increase or decrease a speed of the carrier motion. In some embodiments, the endoscopic deployment device 500 may include at least one vibration motor 531 configured to generate vibrations as an angular position of the motor 512, 522 changes to provide haptic feedback to the user. When using a powered accessory and/or device, tactile feedback normally associated with manual operations may not be available or felt by the user. Haptic feedback provided in accordance with the disclosure addresses the loss of tactile feedback associated with using powered accessories and/or devices, thereby restoring feedback to the user. The at least one vibration motor 531 may be positioned in proximity to (e.g., attached to, disposed under, etc.) the one or more actuation buttons 530 such that the user can feel the vibrations generated by the vibration motor 531 with the user's finger contacting the associated actuation button 530. In at least one embodiment, each of the one or more actuation buttons 530 may have one corresponding and/or adjacent vibration motor 531. In other embodiments, the vibration motor(s) 531 may be positioned at a different location of the endoscopic deployment device 500, if desired. In some instances, the user can detect an audible change in tone/sound resonating from the vibration motor(s) 531 to provide feedback. In some embodiments, the endoscopic deployment device 500 may include a vibration motor control board 511 configured to control the at least one vibration motor 531 in response to signals from the one or more actuation buttons 530 and/or the position of the carrier 516. In some embodiments, the control board 510 may also control the at least one vibration motor 531.

In some embodiments, an intensity of the vibrations corresponds to the angular position of the motor 512, 522 and/or the linear position of the carrier 516. Thus, the intensity of the vibrations may correspond with the degree that the end effector is open or closed. In some embodiments, the intensity of the vibrations is non-linear relative to the angular position of the motor 512, 522, as illustrated in FIG. 15 for example. In some embodiments, the intensity of the vibrations is linear relative to the angular position of the motor 512, 522, as illustrated in FIG. 16 for example.

Placement of the one or more actuation buttons 530 adjacent to the grip area 118 and/or deflection knob 116 of the endoscopic device 100 (e.g., when the endoscopic deployment device 500 is attached, coupled, and/or mounted to the handle 102 of the endoscopic device 100) provides ergonomic benefits to the user of the devices. For example, a typical user may have difficulty operating an endoscopic deployment device and a distal tip deflection mechanism simultaneously, especially when the thumb is extended on the deflection knob 116 at full deflection, and especially if the user has a small hand. The spatial configuration of the endoscopic device 100 and the endoscopic deployment device 500 allow for ease of use due to the proximity of the one or more actuation buttons 530, the deflection knob 116, and/or the grip area 118.

Figure 6:
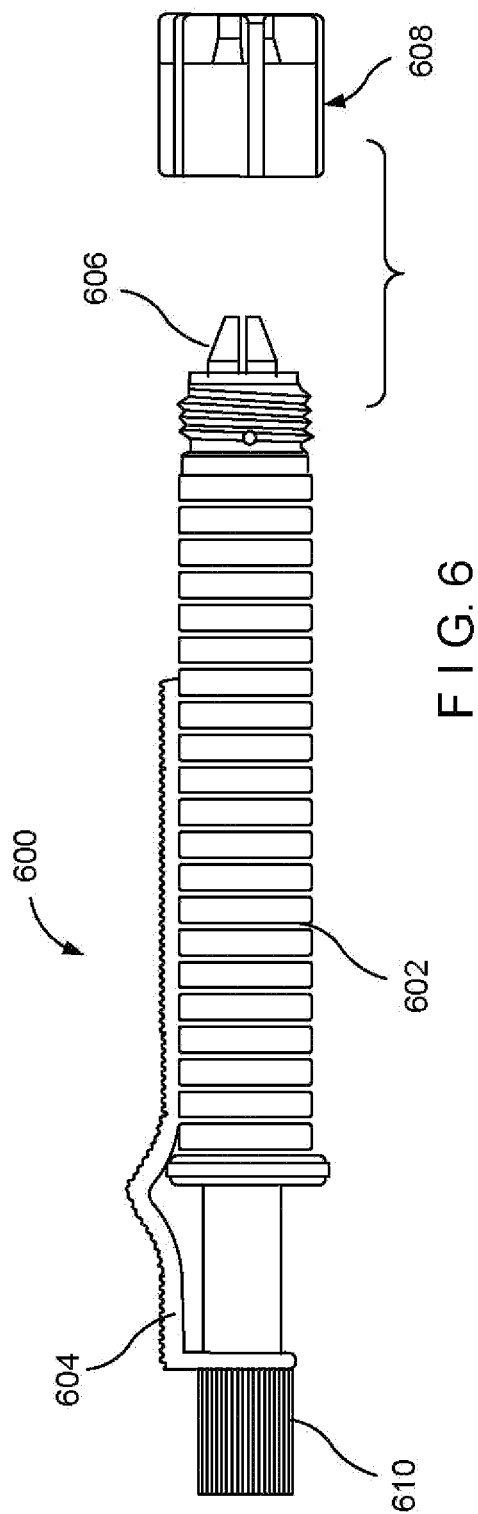
FIG. 6 shows an exemplary handle compatible with the motorized deployment devices of FIGS. 4A-5B and an elongated end effector device.
Figure 7A:
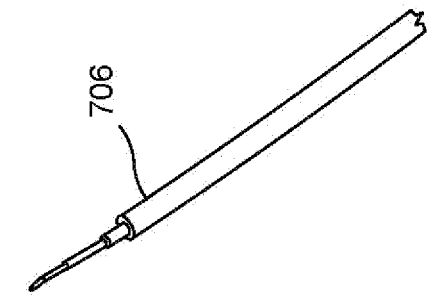
FIGS. 7A-7F show exemplary elongated end effector devices compatible with a handle.
Figure 7B:
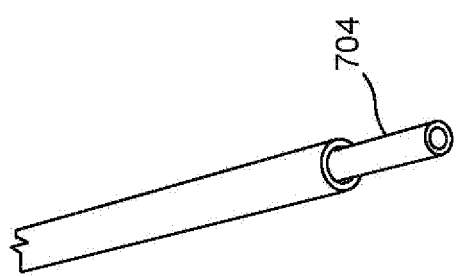
Figure 7C:
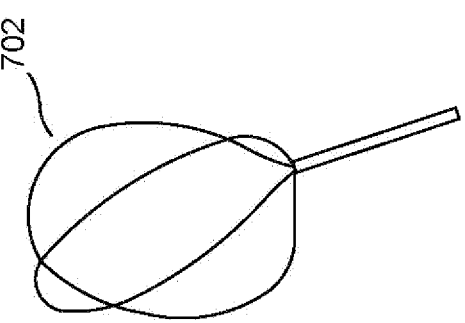
Figure 7D:
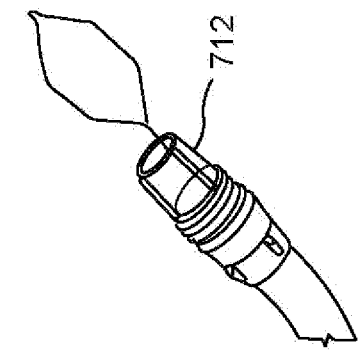
Figure 7E:
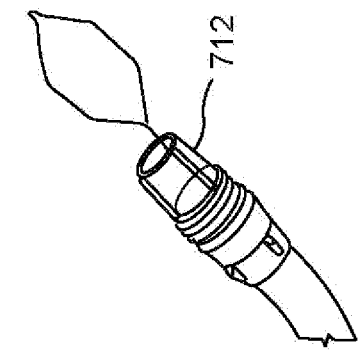
Figure 7F:
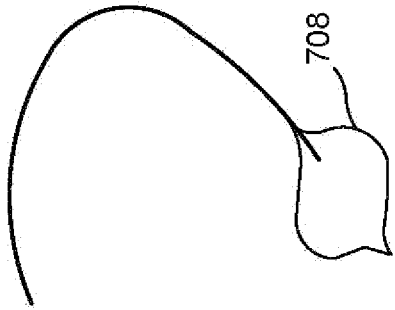

FIG. 6 shows an exemplary handle 600 that may be fitted to any of the aforementioned elongated end effector devices. In some embodiments, the handle 600 may be either of a Segura™ or a Dakota™ handle, depending on the elongated end effector device to which it is fitted, or may be a similar device for actuating an end effector device. Other configurations are also contemplated.

The handle 600 has a body 602 over which a slide 604 may slide. A male luer 610 is attached to a distal end of the slide 604, while a shaft, i.e. pull wire of the elongated end effector device is held by a jaw vise including a plurality of jaws 606 at a proximal end 605 of the body 602. A cap 608 forces the plurality of jaws 606 closed around the shaft of the end effector device as the cap 608 is screwed onto the body 602. The body 602 has a through-lumen (not pictured) for the shaft of the elongated end effector device. Thus, it may be seen that the slide 604 may move relative to the body 602 and the shaft of the elongated end effector device. An outer sheath of the end effector device is connected vis a female luer to the male luer 610 and extends to cover the end effector at the distal end of the end effector device. When the slide 604 is moved distally it in turn moves the outer sheath distally over the end effector to close the end effector, and when the slide 604 is moved proximally it in turn moves the outer sheath proximally to uncover the distal end of the end effector, causing the self-opening, memory set end effector to open. A stroke-limiter in the handle 600 may govern the travel of the slide 604 relative to the end effector size.

As discussed previously, the carriers 416, 516 of the endoscopic deployment devices 400, 500 are, in these embodiments, sized and shaped for compatibility with the slide 604 of the handle 600. Thus, when the endoscopic deployment device 400, 500 is actuated to move the carrier 416, 516 in a proximal or distal direction, the slide 604 is correspondingly moved with respect to the body 602 and the end effector of the end effector device is moved towards the extended open position or moved towards the retracted closed position.

FIGS. 7A-F show examples of elongated end effector devices compatible with the handle 600, including a stone/particle retrieval basket. FIGS. 7A-7F show: a retrieval basket or device 702 for capturing objects at a distal end of the endoscopic shaft, a laser fiber device 704 for fragmenting and/or cauterizing objects at the distal end of the endoscopic shaft, a therapy needle 706 for puncturing and/or supplying medicament to a treatment site, a snare 708 for capturing objects at the distal end of the endoscopic shaft, a forceps 710 for capturing and/or grasping objects at the distal end of the endoscopic shaft, and a band ligation device 712, respectively. Each of the elongated end effector devices may be fitted with the handle 600 and may be operated by the endoscopic deployment device 400 and/or the endoscopic deployment device 500.

The motors 412, 512, 522 described with respect to the endoscopic deployment devices 400 and 500 may be, e.g., a DC motor, a servo motor, a stepper motor, or the like. The preferred embodiment for the motor 412, 512, 522 is the stepper motor. A stepper motor is a brushless electromechanical device that converts the train of electric pulses applied at their excitation windings into precisely defined step-by-step mechanical shaft rotation. The shaft of the motor rotates through a fixed angle for each discrete pulse, which may be translated to linear motion in any of the aforementioned ways. Each pulse provides one step of motion, i.e., the angle through which the stepper motor shaft turns for each pulse is referred to as the step angle, generally expressed in degrees. The position of the motor shaft is controlled by controlling the number of pulses. This feature makes the stepper motor to be well suited for an open-loop control system wherein the precise position of the shaft is maintained with an exact number of pulses without using a feedback sensor. If the step angle is smaller, the greater will be the number of steps per revolution and the higher will be the accuracy of the position obtained. The step angles can be as large as 90 degrees and as small as 0.72 degrees, however, the commonly used step angles are 1.8 degrees, 2.5 degrees, 7.5 degrees and 15 degrees. The direction of the shaft rotation depends on the sequence of pulses applied to the stator. The speed of the shaft or the average motor speed is directly proportional to the frequency (the rate of input pulses) of input pulses being applied at excitation windings. Therefore, if the frequency is low, the stepper motor rotates in steps and for high frequency, it continuously rotates like a DC motor due to inertia. Stepper motors continue to generate holding torque even at standstill. This means that the motor can be held at a stopped position without using a mechanical brake. The built-in pulse generation function (controller) allows the stepper motor to be driven via a directly connected personal computer, programmable controller or console. The stepper motor may achieve precise positioning via digital control, such control to be explained in further detail below.

Figure 8:
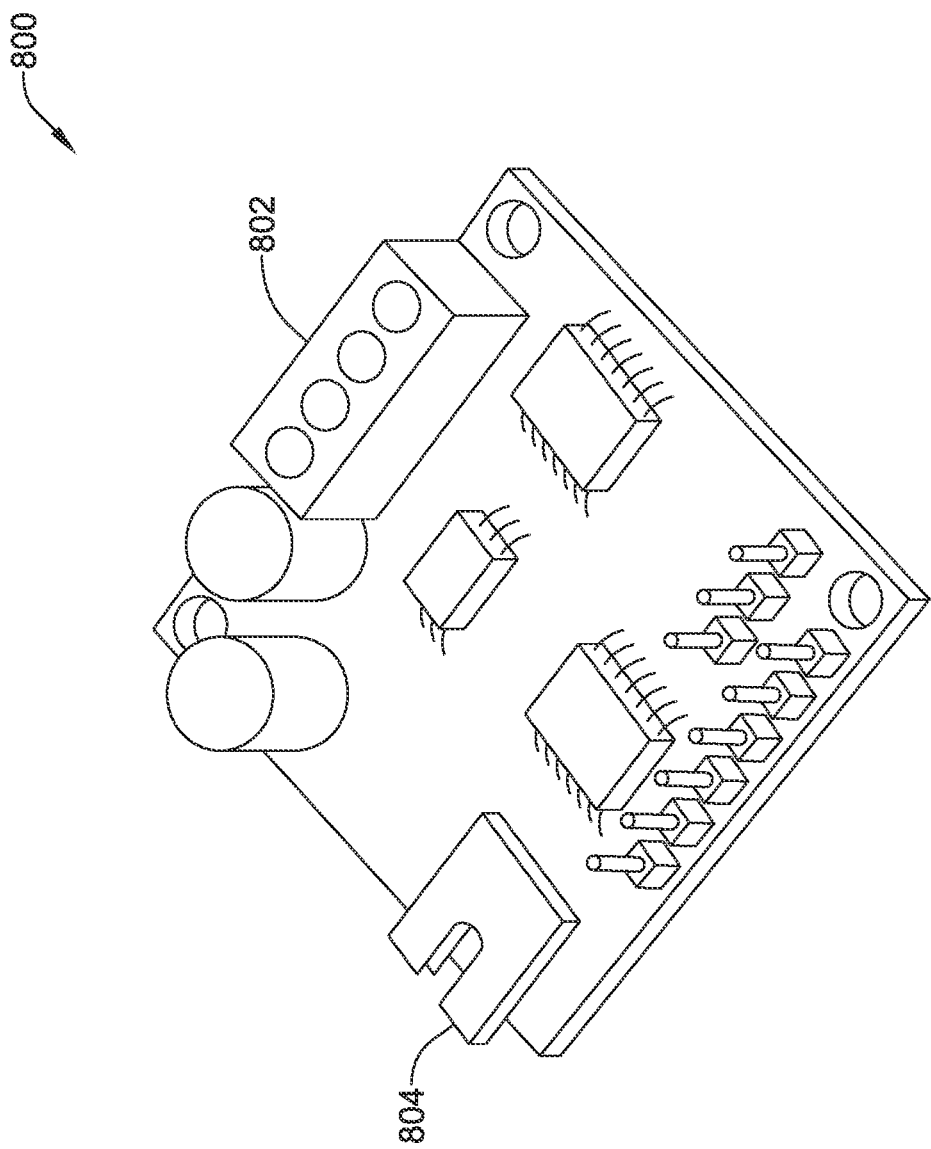
FIG. 8 shows a stepper motor control board.

FIG. 8 shows an example stepper motor control board 800. The stepper motor control board 800 comprises a USB port 804 for connecting a USB cable and motor terminals 802 for connecting a stepper motor. The stepper motor control board 800 may be used in either of the endoscopic deployment devices 400, 500 as the control board 410 for the motor 412 or the control board 510 for the motor 512, 522, when those motors are stepper motors. However, if a stepper motor is not used, the corresponding control board is configured to drive whichever motor type is used. For example, if the motor 412 is a servo motor, the control board 410 is a servo motor control board. The motor control board may be custom built. The motor may be powered via the USB port 804, however, in another embodiment, the motor may be powered by batteries. Other configurations are also contemplated.

Different elongated end effector devices may be implemented in the endoscopic deployment device 400 or 500, each one having a distinct data set for controlling the end effector. For example, each end effector device may have different stop limits or stroke lengths for the carrier 416, 516. However, through the "plug-and-play" functionality of the endoscopic device 100, the data sets may be automatically loaded to the controller. Alternately, a type of elongated end effector device may be selected through a drop-down menu on the console. To assemble the handle 600 to the endoscopic deployment device 400, 500, the carrier 416, 516 is moved to its most proximal position, (e.g., by depressing one of the one or more actuation buttons 430, 530, by depressing the actuation button 1203 of FIG. 12, by depressing the second actuation button 1212 of FIG. 12A, etc.), and the slide of the handle 600 is also moved to the most proximal position. This would match the contours of the slide and carrier such that the handle 600 is aligned and can be snapped into the endoscopic deployment device 400, 500. Actuation button 1204 of FIG. 12 or the first actuation button 1210 of FIG. 12A, for example, is depressed to close or retract the end effector before the end effector is inserted into the working channel of the endoscopic device 100. To remove the elongated end effector device, the end effector is closed by depressing e.g. the actuation button 1204 or the first actuation button 1210. The end effector shaft of the elongated end effector device is withdrawn and the handle 600 can be unclipped from the endoscopic deployment device 400, 500 and put aside for later use. Another elongated end effector device can be quickly exchanged for the previous elongated end effector device to perform its function.

In an alternate embodiment, the endoscopic device 100 and the endoscopic deployment device 400, 500 may be implemented in a single monolithic unit. In such an embodiment, instead of using mount holes and mount pins to connect the respective devices, the endoscopic deployment device is built into the handle 102 of the endoscopic device 100 and all associated wiring is within the endoscopic device 100.

In at least some embodiments, deflection of the distal tip 106 of the endoscopic device 100 may be motorized/wired using the same control board, such as the control board 800, as the endoscopic deployment device 400, 500. In such an embodiment, a second driver and a second motor would be implemented in the handle 102 for controlling deflection of the distal tip 106.

Figure 9:
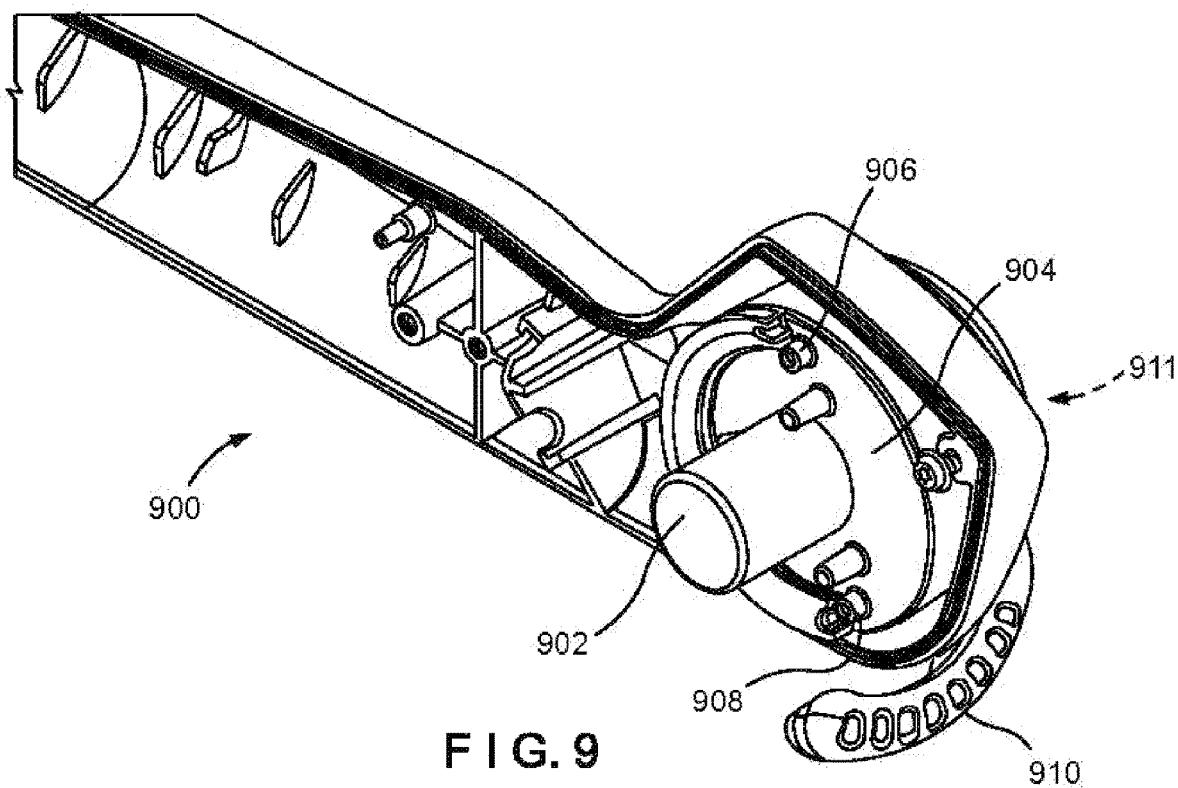
FIG. 9 shows a handle of an endoscopic device with a motor for controlling the deflection of a distal tip.

FIG. 9 shows a handle 900 of the endoscopic device 100 with a motor 902 for controlling deflection of the distal tip 106. The endoscopic device 100 in this embodiment may have two pull wires (not shown) for deflecting the distal tip 106 in either of two opposing directions (e.g., up and down, left and right, etc.). A pull wire wheel 904 has a first pull wire attachment 906 and a second pull wire attachment 908. The motor 902 is mounted in the handle 900 with its drive shaft mounted in the center of the pull wire wheel 904. In at least some embodiments, the motor 902 may be a stepper motor. A lever 910 may be coupled to the handle 900, and may be keyed to the rotation of the pull wire wheel 904 via a controller/driver and wiring (not shown). The lever 910 may be and/or correspond to the deflection knob 116 of the endoscopic device 100. Thus, the lever 910 may operate as a switch and rotate independently from the pull wire wheel 904. When pressure is applied on the lever 910 in a first direction, the motor 902 will rotate the pull wire wheel 904 such that one of the two pull wires, e.g. the pull wire attached to the first pull wire attachment 906, pulls the distal tip 106 of the endoscopic device 100 in one of the two directions. Similarly, when pressure is applied on the lever 910 in the second direction, the motor 902 will rotate the pull wire wheel 904 such that the second of the two pull wires, e.g., the pull wire attached to the second pull wire attachment 908, pulls the distal tip 106 of the endoscopic device 100 in the second of the two directions. Release of the lever 910 may stop the motor 902, allowing the then-current position of the distal tip 106 to be maintained. The maximum angular travel of the motor 902 will be set to the limitations of the distal tip deflection. In some embodiments, the distal tip 106 may be deflectable 270 degrees in either (or both) of the two opposing directions. In some embodiments, a first vibration motor 911 may be disposed within the handle 900 proximate the lever 910 such that the user can feel the vibrations generated by the vibration motor 911 with the user's finger contacting the associated lever 910. For example, the first vibration motor 911 may be coupled to the lever 910, may be disposed under the lever 910, may be disposed within the lever 910, etc. The first vibration motor 911 may be configured to generate vibrations within the lever 910 as an angular position of the motor 902 within the handle 900 changes. In other embodiments, the vibration motor 911 may be positioned at a different location of the endoscopic deployment device 900, if desired. In some instances, the user can detect an audible change in tone/sound resonating from the vibration motor 911 to provide feedback.

In some embodiments, an intensity of the vibrations corresponds to the angular position of the motor 902. Thus, the intensity of the vibrations may correspond with the degree of angulation of the distal tip 106 away from a central longitudinal axis of the endoscopic shaft 104. In some embodiments, the intensity of the vibrations is non-linear relative to the angular position of the motor 902, as illustrated in FIG. 15 for example. In some embodiments, the intensity of the vibrations is linear relative to the angular position of the motor 902, as illustrated in FIG. 16 for example. For example, the intensity of the vibrations within the lever 910 may change (e.g., increase or decrease) as deflection of the distal tip 106 away from a central longitudinal axis of the endoscopic shaft 104 changes (e.g., increases or decreases). For instance the intensity of the vibrations may increase as the degree of angulation of the distal tip 106 increases. Thus, the intensity of the vibrations may provide the user with hepatic feedback regarding the degree of angulation of the distal tip 106.

Figure 10A:
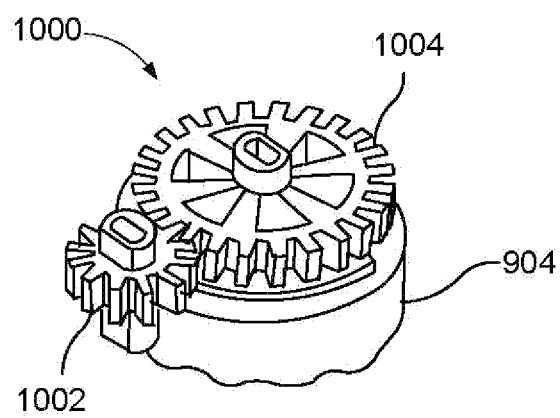
FIGS. 10A-C show a gear train for driving a pull wire wheel of the device of FIG. 9.
Figure 10B:
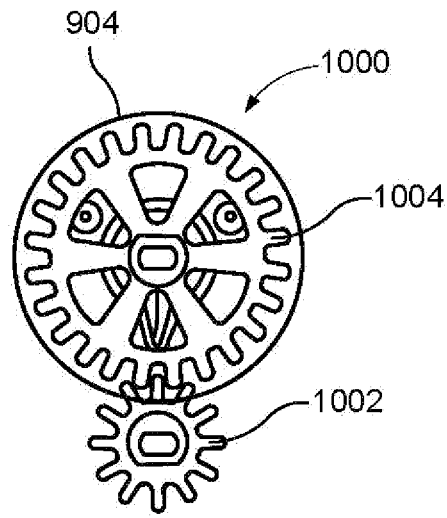
Figure 10C:
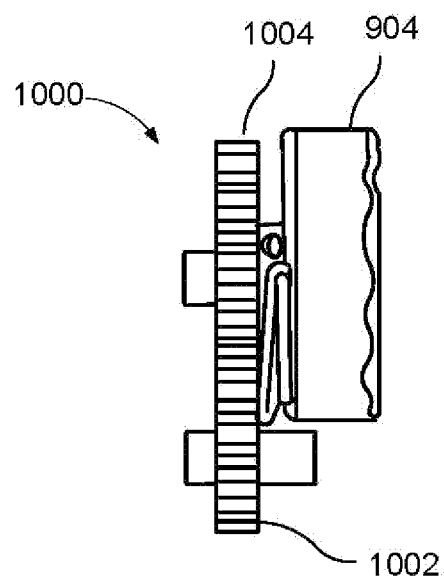
Figure 10D:
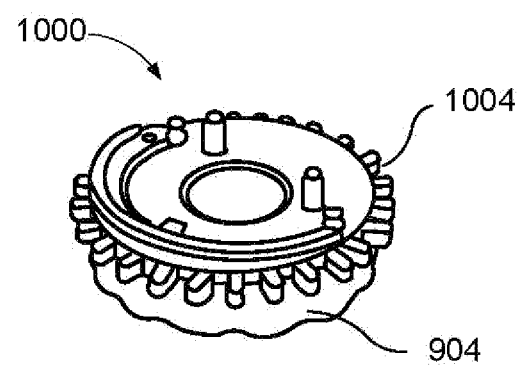
FIG. 10D shows the pull wire wheel of the device of FIG. 9 fashioned with a gear.
Figure 11:
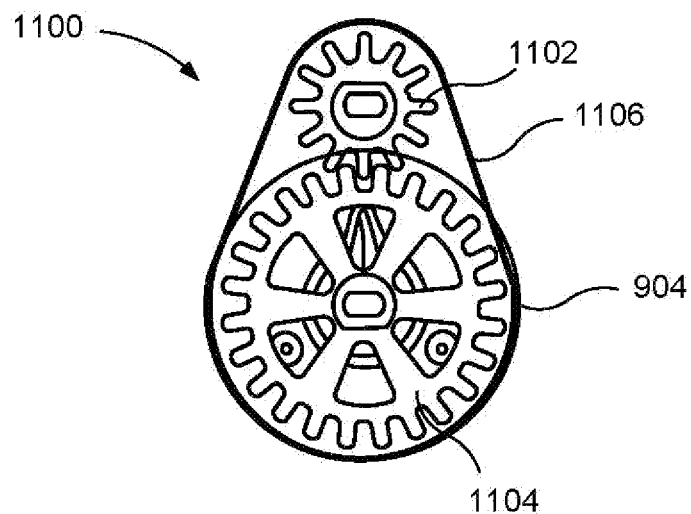
FIG. 11 shows the gear train of FIGS. 10A-C with a pulley.

In some embodiments, a gear train may be used in the handle 900 between the motor 902 and the pull wire wheel 904, instead of the motor 902 driving the pull wire wheel 904 directly. FIGS. 10A-C show a simple two-gear train 1000 where a smaller gear 1002 drives a larger gear 1004 that rotates the pull wire wheel 904. The larger gear 1004 and the pull wire wheel 904 may be fashioned as a single part where the gear teeth extend from the circumference/perimeter of the pull wire wheel 904, as shown in FIG. 10D. FIG. 11 shows a two-gear train 1100 with a smaller gear 1102 and a larger gear 1104 comprising a pulley belt 1106. The mechanical advantage of the aforementioned embodiments is to use a less powerful and/or less expensive motor 902. In some embodiments of the endoscopic device 100 and/or the handle 900, driving the pull wire wheel 904 directly will require a higher torque specification for the motor 902 than would be needed using the gear train 1000, 1100 shown in FIGS. 10-11.

The aforementioned aspects of the present disclosure may be combined in various ways. In some embodiments, both the distal tip 106 of the endoscopic device 100 and the endoscopic deployment device 400, 500 are motorized.

Figure 12:
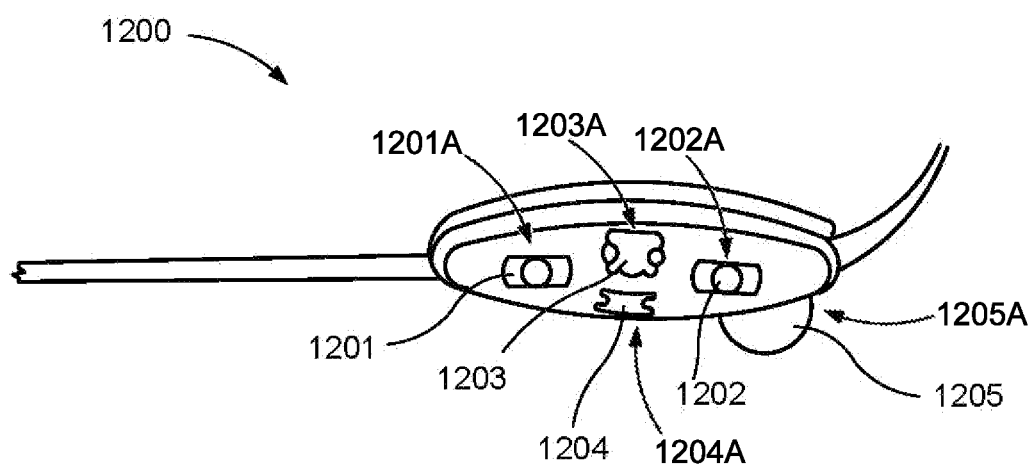
FIG. 12 shows an ergonomic button pad for controlling a scope tip and an elongated end effector device.

In some embodiments, the one or more actuation buttons described herein may be a button pad 1200 physically separate from the body of the endoscopic deployment device 400, 500 and in operable communication with the motor 412, 512, 522. FIG. 12 illustrates an ergonomic button pad 1200 for controlling the distal tip 106 of the endoscopic device 100 and the endoscopic deployment device 400, 500. The button pad 1200 has a first actuation button 1201, a second actuation button 1202, a third actuation button 1203 and a fourth actuation button 1204. The button pad 1200 is also adjacent to a shortened deflection knob 1205, which may be and/or may function as the deflection knob 116 and/or the lever 910. The deflection knob 1205 is shortened to allow the placement of the button pad 1200 adjacent to the deflection knob 1205. In other embodiments, the deflection knob 1205 may be eliminated completely, with deflection of the distal tip 106 of the endoscopic device 100 being controlled by the button pad 1200. In another embodiment, the shortened deflection knob 1205 may be used as a safety/bailout feature in case of e.g. power failure, considering the deflected distal tip 106 has to be straightened before it can be removed from the body without injuries.

The button pad 1200 is connected to a controller programmed for all aspects of the intervention. The button pad 1200 is located on and/or adjacent to the bottom side of the handle 102 and may be operated, for example, by the thumb of the scope handle grip hand. For example, the first actuation button 1201 and the second actuation button 1202 (opposite one another; e.g., distal button and proximal button, respectively, in FIG. 12) may be used to deflect the distal tip 106 in either of the two opposing directions. For example, the first actuation button 1201 may be configured to deflect the distal tip 106 downward relative to the central longitudinal axis of the endoscopic shaft 104, and the second actuation button 1202 may be configured to deflect the distal tip 106 upward relative to the central longitudinal axis of the endoscopic shaft 104. Other configurations are also contemplated, including the first and second actuation buttons 1201, 1202 being configured to operate the distal tip 106 in directions opposite those described above. In some embodiments, the third actuation button 1203 and the fourth actuation button 1204 (opposite one another; e.g., upper button and lower button, respectively, in FIG. 12) may be used to move the carrier 416, 516 proximally and distally, respectively, to thereby control opening and closing, respectively, of the elongated end effector device. In some embodiments, a fifth actuation button may be implemented, such that when the fifth button is "on," the third actuation button 1203 and the fourth actuation button 1204 are used to turn on and off a fluid management system to flush the imaged cavity. Alternatively, the fifth actuation button alone may actuate and/or engage and disengage the fluid management system. In some embodiments, the button pad 1200 may be programmed such that the microprocessor is executing the direction of movement of the motor 412, 512, 522 and/or the motor 902 via a program, when a conditional statement in the program is true.

In at least some embodiments, the button pad 1200 may include a first vibration motor 1201A associated with the first actuation button 1201, a second vibration motor 1202A associated with the second actuation button 1202, a third vibration motor 1203A associated with the third actuation button 1203, and a fourth vibration motor 1204A associated with the fourth actuation button 1204. More or fewer vibration motors may also be used in some configuration. For example, only one vibration motor may be used with each related pair of actuation buttons (e.g., buttons 1201/1202, buttons 1203/1204). Similarly, at least one vibration motor 1205A may be associated with the deflection knob 1205 as described herein with respect to the deflection knob 116 and/or the lever 910.

In another embodiment, the handle 102 of the endoscopic device 100 and the body of the endoscopic deployment device 400, 500 may be arranged and/or constructed such that all controls are disposed in and/or on the handle 102. For example, the endoscopic deployment device 400 may be mounted on the handle 102 of the endoscopic device 100. In another example, the endoscopic deployment device 400 may be monolithically formed with the handle 102. In one example shown in FIG. 12A, rotation of the drive shaft slides the carrier in the carrier channel and actuates the end effector of the elongated end effector device in response to a signal from one or more actuation buttons on the handle 102. The description relative to the endoscopic deployment device 400 may be equally applied with respect to the endoscopic deployment device 500. Similar to other embodiments described herein, the handle 102 of the endoscopic device 100 may include a deflection knob 1205 (e.g., deflection knob 116 and/or lever 910). A first vibration motor 1205A may be configured to generate vibrations within the deflection knob 1205 (and/or the deflection knob 116, and/or the lever 910, where so equipped) as an angular position of the motor (not shown) within the handle 102 changes such that the user can feel the vibrations generated by the vibration motor 1205A with the user's finger contacting the associated deflection know 1205 (and/or the deflection knob 116 and/or the lever 910, where so equipped). In other embodiments, the vibration motor 1205A may be positioned at a different location of the endoscopic 100, if desired. In some instances, the user can detect an audible change in tone/sound resonating from the vibration motor 1205A to provide feedback. Similar to above and/or other embodiments herein, an intensity of the vibrations within the deflection knob 1205 (and/or the deflection knob 116, and/or the lever 910, where so equipped) increases as deflection of the distal tip 106 away from the central longitudinal axis of the endoscopic shaft 104 increases and/or approaches its deflection limit (e.g., its most deflected position). Thus, the intensity of the vibrations may correspond with the degree of angulation of the distal tip 106 away from a central longitudinal axis of the endoscopic shaft 104.

Figure 12A:
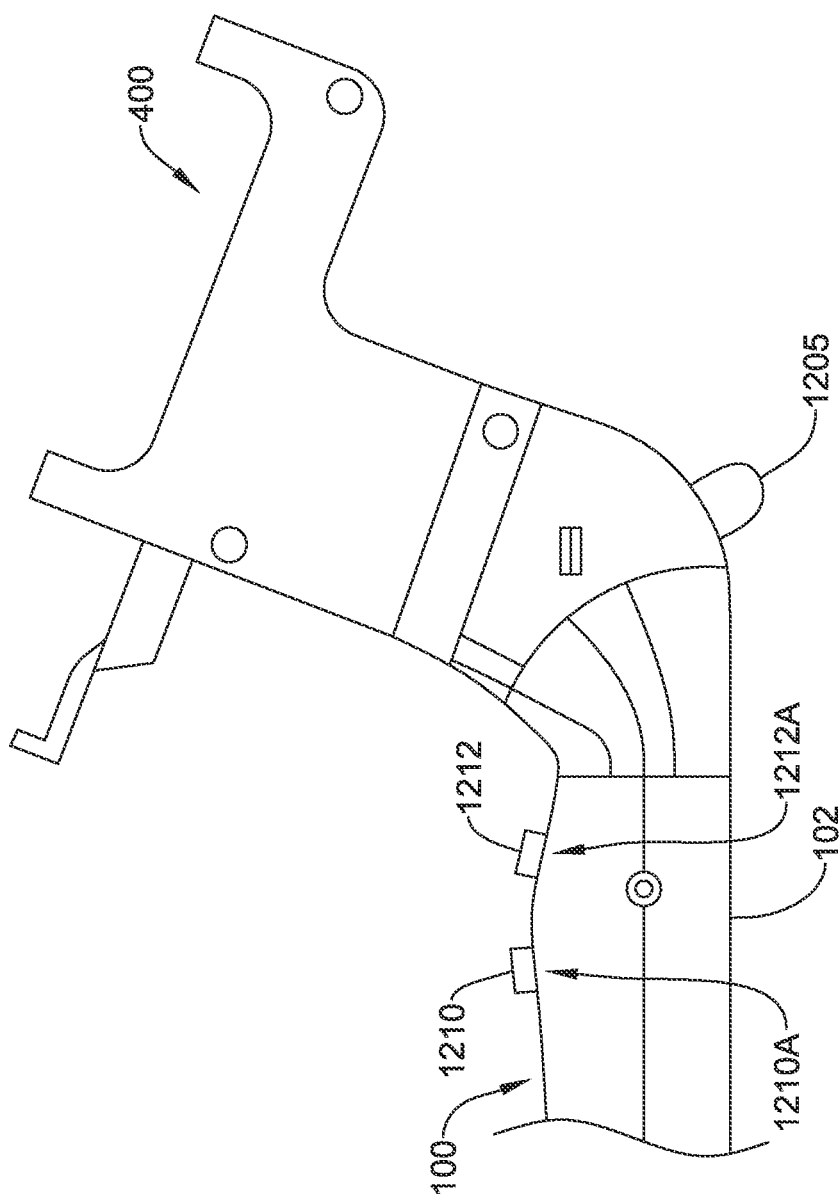
FIG. 12A shows a portion of a handle of an endoscopic device with a motorized deployment device mounted on the handle.

In the example shown in FIG. 12A, the handle 102 may further include at least one vibration motor configured to generate vibrations within the one or more actuation buttons as an angular position of the motor 412 (not visible) within the body of the endoscopic deployment device 400 changes. In some embodiments, the at least one vibration motor may include a second vibration motor 1210A associated with (e.g., coupled to, disposed under, etc.) a first actuation button 1210 of the one or more actuation buttons and a third vibration motor 1212A associated with (e.g., coupled to, disposed under, etc.) a second actuation button 1212 of the one or more actuation buttons. In some embodiments, the second vibration motor 1210A may be configured to generate vibrations within the first actuation button 1210 when the end effector is actuated toward the retracted closed position (e.g., when the carrier is translated distally). In some embodiments, the third vibration motor 1212A may be configured to generate vibrations within the second actuation button 1212 when the end effector is actuated toward the extended open position (e.g., when the carrier is translated proximally). In some embodiments, an intensity of the vibrations within the first actuation button 1210 increases as the end effector approaches the retracted closed position (and/or as the carrier approaches its most distal position). In some embodiments, an intensity of the vibrations within the second actuation button 1212 increases as the end effector approaches the extended open position (and/or as the carrier approaches its most proximal position.

In another embodiment, the button pad 1200 and/or the actuation buttons 1210, 1212 are implemented on a console, tablet (e.g., iPad) or the like and controlled remotely. Thus, the endoscopic device may be fashioned without control features implemented directly thereon, and may instead be controlled via Bluetooth, infrared remote, etc.

Figure 13:
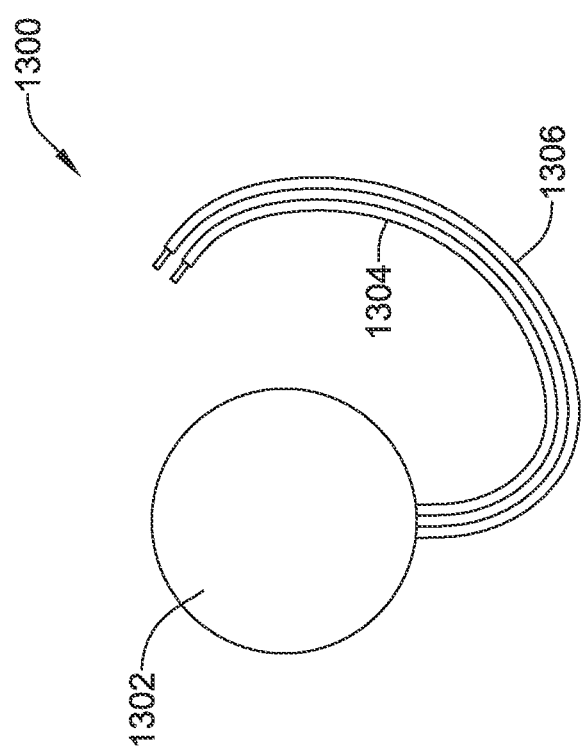
FIG. 13 illustrates an example vibration motor.

FIG. 13 illustrates an example vibration motor 1300 that may be used with the current disclosure. The vibration motor 1300 may include a housing 1302 and connection wires 1304, 1306. In at least some embodiments, the vibration motor 1300 may be shaftless. In some embodiments, the vibration motor may include a flat coreless coil and/or a commutator disposed within the housing 1302. All moving parts may be contained within the housing 1302. In one example, the vibration motor 1300 may operate between 2 volts and 3.6 volts and may operate at about 13,000+/−3000 rpm. Other configurations and/or arrangements are also contemplated. None, any, and/or all of the vibration motors described herein may be the vibration motor 1300.

Figure 14:
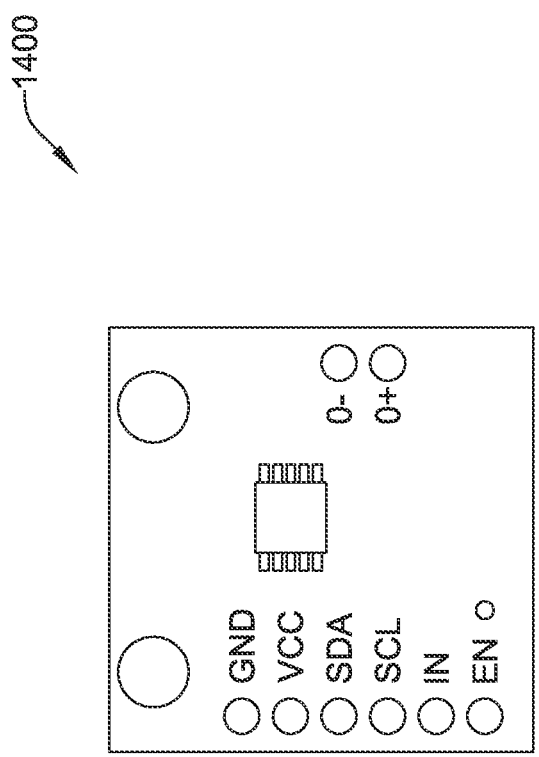
FIG. 14 illustrates an example vibration motor control board.

FIG. 14 illustrates an example vibration motor control board 1400 for use with the vibration motor 1300. In some embodiments, the vibration motor control board 1400 may be a haptic motor driver configured to control the vibration motor 1300. In the illustrated example, the vibration motor control board 1400 includes six pins to provide power and communication to the vibration motor control board 1400. The vibration motor control board 1400 may include built-in firmware for driving the vibration motor 1300. In one example, the vibration motor control board 1400 may operate between 2 volts and 5.2 volts. Other configurations are also contemplated. In some embodiments, none, any, and/or all of the vibration motor control boards 411, 511 may be the vibration motor control board 1400. Additionally, in some embodiments, control of the vibration motor 1300 may be built into the motor control boards 410, 510 and thus a dedicated vibration motor control board 1400 is not needed.

FIG. 15 illustrates a graph showing vibration intensity of the vibrations produced by the vibration motor 1300 (and/or any of the vibration motors described herein) relative to degrees of rotation of the associated motor (e.g., any one or more of the motors 412, 512, 522, 902). As shown, in some embodiments, the intensity of the vibrations is non-linear relative to the angular position of the motor. For example, a map of the intensity of the vibrations may lie along a parabolic curve and/or may be exponential in nature. In FIG. 15, a horizontal axis 1504 shows degrees of rotation (e.g., angular position) of the motor relative to a central starting position (e.g., 0 degrees). In accordance with selected embodiments described herein, the motor may be actuatable and/or movable between −270 degrees and +270 degrees relative to the central starting position. In FIG. 15, a vertical axis 1502 shows relative intensity of the vibrations as a percentage of the intensity the vibration motor 1300 is capable of producing. The intensity of the vibrations may increase as the angular position of the motor away from a neutral position (e.g., 0 degrees) increases. The values illustrated are merely exemplary, and other configurations are also contemplated. As shown, as the angular position of the motor moves further away from the central starting position (in either direction), the intensity of the vibrations increases.

FIG. 16 illustrates a graph showing vibration intensity of the vibrations produced by the vibration motor 1300 (and/or any of the vibration motors described herein) relative to degrees of rotation of the associated motor (e.g., any one or more of the motors 412, 512, 522, 902). As shown, in some embodiments, the intensity of the vibrations is linear relative to the angular position of the motor. For example, a map of the intensity of the vibrations may lie along a straight line angled up from a horizontal axis and away (left and right) from a vertical axis. In FIG. 16, the horizontal axis 1604 shows degrees of rotation (e.g., angular position) of the motor relative to a central starting position (e.g., 0 degrees). In accordance with selected embodiments described herein, the motor may be actuatable and/or movable between −270 degrees and +270 degrees relative to the central starting position. In FIG. 16, a vertical axis 1602 shows relative intensity of the vibrations as a percentage of the intensity the vibration motor 1300 is capable of producing. The intensity of the vibrations may increase as the angular position of the motor away from a neutral position (e.g., 0 degrees) increases. The values illustrated are merely exemplary, and other configurations are also contemplated. As shown, as the angular position of the motor moves further away from the central starting position (in either direction), the intensity of the vibrations increases.

In some embodiments, the present disclosure relates to an endoscopic deployment device which includes a body mountable on an endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through a working channel of an endoscopic shaft of the endoscopic device, the body having a carrier channel sized for the carrier to slide therein, wherein the end effecter is actuatable between an extended open position and a retracted closed position by sliding the carrier in the carrier channel which in turn slides the outer sheath over the end effector shaft to uncover or cover the end effector; a communication interface extending from the body and configured to be mated with a corresponding communication interface on the endoscopic device on which the body is mounted to receive power therefrom and exchange data therewith; and a motor having a drive shaft coupled to the carrier, rotation of the drive shaft sliding the carrier in the carrier channel and actuating the end effector in response to a signal.

In an embodiment, the signal is generated based on actuation of an actuator on the endoscopic device.

In an embodiment, the actuator is a button pad controlling the motor via the mated communication interfaces of the endoscopic deployment device and the endoscopic device.

In an embodiment, the signal is generated in response to an endoscopic sensor reading.

In an embodiment, the motor is a stepper motor.

In an embodiment, the drive shaft has an arm extending orthogonally therefrom coupled to a slot in the carrier and the arm has a pin at an end of the arm opposite the drive shaft, the pin being coupled to the slot so that, when the drive shaft rotates, the pin slides in the slot in a direction orthogonal to the carrier channel and the carrier slides in the carrier channel.

In an embodiment, the drive shaft is a lead screw coupled to a threaded through-hole extending through a portion of the carrier parallel to the carrier channel so that, when the drive shaft rotates, the carrier slides in the carrier channel.

In an embodiment, a pinion gear is coupled to the drive shaft and to a rack that is an integral portion of the carrier so that, when the drive shaft rotates, the pinion gear drives the rack and the carrier slides in the carrier channel.

In an embodiment, the end effector device is a retrieval device for capturing objects at a distal end of the endoscopic shaft.

In an embodiment, the end effector device is a laser fiber or energy fiber for fragmenting or cauterizing objects at a distal end of the endoscopic shaft.

In an embodiment, the end effector device has a handle for coupling to the carrier of the endoscopic deployment device, wherein the carrier and a slide of the handle are positioned fully proximally prior to attaching the handle to the endoscopic deployment device.

In an embodiment, the endoscopic device has a proximal communication interface and a distal communication interface and the communication interface of the endoscopic deployment device is compatible with the proximal communication interface of the endoscopic device.

In addition, in some embodiments, the present disclosure relates to an endoscopic device which includes an elongated flexible endoscopic shaft including a working channel and a deflectable distal tip, the flexible endoscopic shaft being sized and shaped for insertion to a target site within a living body, the distal tip including a camera; a handle from which the endoscopic shaft extends distally, the handle including a pull wire wheel comprising pull wire attachments from which first and second pull wires extend distally through the endoscopic shaft to the distal tip, rotation of the pull wire wheel deflecting the distal tip by tensioning a first one of the first and second pull wires and slacking a second one of the first and second pull wires, the handle including an actuator, a proximal end of the handle including a communication interface for connecting an accessory device; and a motor including a rotatable drive shaft coupled to and configured to rotate the pull wire wheel in response to a signal.

In an embodiment, the deflection knob operates as a switch so that deflecting the deflection knob in a first direction rotates the pull wire wheel a predefined angular extent to apply tension to the first one of the first and second pull wires and deflecting the deflection knob in a second direction rotates the pull wire wheel a predefined angular extent to apply tension to the second one of the first and second pull wires.

In an embodiment, the signal is generated by a button pad on an exterior of the handle.

Furthermore, in some embodiments, the present invention relates to a method which includes attaching an endoscopic deployment device to an endoscopic device, the endoscopic deployment device comprising a body mountable on the endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through a working channel of an endoscopic shaft of the endoscopic device, the body having a carrier channel sized for the carrier to slide therein, wherein the end effecter is actuatable between an extended open position and a retracted closed position by sliding the carrier in the carrier channel which in turn slides the outer sheath over the end effector shaft to uncover or cover the end effector, the endoscopic deployment device further comprising a communication interface extending from the body and configured to be mated with a corresponding communication interface on the endoscopic device on which the body is mounted to receive power therefrom and exchange data therewith, the endoscopic deployment device further comprising a motor having a drive shaft coupled to the carrier; and actuating the motor in response to a signal, the actuation of the motor rotating the drive shaft and sliding the carrier in the carrier channel to actuate the end effector.

In an embodiment, the actuator is a button pad on the endoscopic device, the button pad being operated with a thumb of a grip hand of a user.

In an embodiment, the button pad further actuates a deflection of a distal end of the endoscopic shaft.

In an embodiment, the motor is a stepper motor.

In an embodiment, the end effector device is a retrieval device for capturing objects at a distal end of the endoscopic shaft.

The materials that can be used for the various components of the endoscopic device, the endoscopic deployment device, the end effector device, and the various elements thereof disclosed herein may include those commonly associated with medical devices. For simplicity purposes, the following discussion makes reference to the endoscopic device and/or the endoscopic deployment device. However, this is not intended to limit the devices and methods described herein, as the discussion may be applied to other elements, members, components, or devices disclosed herein, such as, but not limited to, the expandable framework, the endoscopic shaft, the distal tip, the handle, the body, the carrier, motor, the drive shaft, the vibration motor (s), the actuation button(s), the button pad, the end effector shaft, the end effector, the outer sheath, etc. and/or elements or components thereof.

In some embodiments, the endoscopic device and/or the endoscopic deployment device, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the endoscopic device and/or the endoscopic deployment device, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the endoscopic device and/or the endoscopic deployment device in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the endoscopic device and/or the endoscopic deployment device to achieve the same result.

In some embodiments, a degree of Magnetic Resonance Imaging (MRI) compatibility is imparted into the endoscopic device and/or the endoscopic deployment device and/or other elements disclosed herein. For example, the endoscopic device and/or the endoscopic deployment device, and/or components or portions thereof, may be made of a material that does not substantially distort the image and create substantial artifacts (i.e., gaps in the image). Certain ferromagnetic materials, for example, may not be suitable because they may create artifacts in an MRI image. The endoscopic device and/or the endoscopic deployment device, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

The invention claimed is:

1. An endoscopic deployment device, comprising:
    a body couplable to a handle of an endoscope, the body having a channel and a carrier translatable within the channel;
    wherein the body is configured to receive an end effector device handle of an end effector device having an end effector device shaft extending from the end effector device handle and configured for insertion through a working channel of the endoscope;
    wherein the carrier is configured to engage with the end effector device handle;
    a powered motor coupled to the body, wherein rotation of the powered motor is configured to translate the carrier within the channel to actuate the end effector device; and
    at least one vibration motor coupled to the body, the at least one vibration motor being configured to generate vibrations as an angular position of the powered motor changes.

2. The endoscopic deployment device of claim 1, wherein the powered motor is configured to rotate in response to signals from one or more actuation buttons.

3. The endoscopic deployment device of claim 2, wherein the one or more actuation buttons is a button pad physically separate from the body and in operable communication with the powered motor.

4. The endoscopic deployment device of claim 1, wherein an intensity of the vibrations corresponds to the angular position of the powered motor.

5. The endoscopic deployment device of claim 4, wherein the intensity of the vibrations is linear relative to the angular position of the powered motor.

6. The endoscopic deployment device of claim 4, wherein the intensity of the vibrations is non-linear relative to the angular position of the powered motor.

7. The endoscopic deployment device of claim 1, wherein the powered motor is a stepper motor.

8. The endoscopic deployment device of claim 1, wherein rotation of the powered motor is configured to translate the carrier within the channel to actuate the end effector device.

9. The endoscopic deployment device of claim 8, wherein an arm extends from the powered motor to the carrier and the arm has a pin at an end of the arm opposite the powered motor, the pin being disposed in a slot formed in the carrier such that rotation of the powered motor slides the pin in the slot in a direction orthogonal to the channel as the carrier translates within the channel.

10. The endoscopic deployment device of claim 8, wherein a lead screw extending from the powered motor is engaged with a threaded through-hole extending through a portion of the carrier parallel to the channel configured such that rotation of the powered motor translates the carrier within the channel.

11. The endoscopic deployment device of claim 8, wherein a pinion gear coupled to the powered motor is engaged with a rack coupled to the carrier such that rotation of the powered motor rotates the pinion gear to drive the rack and translate the carrier within the channel.

12. The endoscopic deployment device of claim 1, wherein the end effector device is a retrieval device for capturing objects at a distal end of the endoscope.

13. The endoscopic deployment device of claim 1, wherein the end effector device is a laser fiber for fragmenting or cauterizing objects at a distal end of the endoscope.

14. An endoscopic system, comprising:
    an endoscope comprising an endoscope handle and a flexible endoscope shaft extending distally from the endoscope handle to a deflectable distal tip;
    wherein the endoscope handle includes a first motor disposed therein, the first motor being configured to deflect the deflectable distal tip in response to a signal from a lever coupled to the endoscope handle; and
    an endoscopic deployment device comprising a body mounted on the endoscope handle, the body having a channel and a carrier translatable within the channel;
    wherein the body is configured to receive an end effector device handle of an end effector device having an end effector device shaft extending from the end effector device handle and configured for insertion through a working channel of the endoscope;
    wherein the carrier is configured to engage with the end effector device handle;
    a powered motor coupled to the body, wherein the powered motor is configured to rotate in response to signals from one or more actuation buttons;
    wherein rotation of the powered motor is configured to translate the carrier within the channel to actuate the end effector device; and
    at least one vibration motor coupled to the body, the at least one vibration motor being configured to generate vibrations as an angular position of the powered motor changes.

15. The endoscopic system of claim 14, wherein the endoscope handle includes a first vibration motor configured to generate vibrations within the lever as an angular position of the first motor changes.

16. The endoscopic system of claim 15, wherein an intensity of the vibrations within the lever increases as deflection of the deflectable distal tip away from a central longitudinal axis of the flexible endoscope shaft increases.

17. The endoscopic system of claim 16, wherein the intensity of the vibrations within the lever is linear relative to the angular position of the first motor.

18. The endoscopic system of claim 14, wherein an intensity of the vibrations within the one or more actuation buttons corresponds to the angular position of the powered motor.

19. The endoscopic system of claim 18, wherein the at least one vibration motor includes a second vibration motor coupled to a first actuation button of the one or more actuation buttons and a third vibration motor coupled to a second actuation button of the one or more actuation buttons.

20. The endoscopic system of claim 19, wherein the first actuation button and the second actuation button are disposed on the endoscope handle.

* * * * *